(12) United States Patent
Lavdas et al.

(10) Patent No.: US 12,222,325 B2
(45) Date of Patent: Feb. 11, 2025

(54) LYMPH NODE LOCATING DEVICE

(71) Applicant: The University of Western Ontario, London (CA)

(72) Inventors: Michael Lavdas, London (CA); Saumik Biswas, London (CA); Elizabeth Pasman, London (CA); Sherif Abdou, London (CA); Gordon Ngo, London (CA); Kirill Fedorov, London (CA); Sejla Abdic, London (CA); Matthew Cecchini, London (CA)

(73) Assignee: The University of Western Ontario, London (CA)

( * ) Notice: Subject to any disclaimer, the term of this patent is extended or adjusted under 35 U.S.C. 154(b) by 0 days.

(21) Appl. No.: 18/579,236

(22) PCT Filed: Jul. 13, 2022

(86) PCT No.: PCT/CA2022/051089
§ 371 (c)(1),
(2) Date: Jan. 12, 2024

(87) PCT Pub. No.: WO2023/283734
PCT Pub. Date: Jan. 19, 2023

(65) Prior Publication Data
US 2024/0319144 A1    Sep. 26, 2024

Related U.S. Application Data

(60) Provisional application No. 63/221,172, filed on Jul. 13, 2021.

(51) Int. Cl.
*G01N 29/265* (2006.01)
*A61B 8/00* (2006.01)
(Continued)

(52) U.S. Cl.
CPC ............ *G01N 29/265* (2013.01); *A61B 8/08* (2013.01); *A61B 8/4209* (2013.01);
(Continued)

(58) Field of Classification Search
CPC ............ G01N 29/265; G01N 29/0654; G01N 33/4833; G01N 2291/0289; G01N 29/225;
(Continued)

(56) References Cited

U.S. PATENT DOCUMENTS 5,678,553 A    10/1997    Uhlendorf et al.

FOREIGN PATENT DOCUMENTS

CA    3224259 A1 *    1/2023    ............ A61B 8/42
WO    2012169543 A1    12/2012
(Continued)

OTHER PUBLICATIONS

International Search Report Mailed Sep. 29, 2022 in International Application PCT/CA2022/051089 filed Jul. 13, 2022.

*Primary Examiner* — Jacques M Saint Surin
(74) *Attorney, Agent, or Firm* — Shook, Hardy & Bacon L.L.P.

(57) ABSTRACT

The system is for use with a tissue sample and includes a tray and an apparatus. The tray is for receiving the tissue sample in use and an apparatus. The apparatus includes: a support which receives the tray in use: a probe adapted to transmit waves and identify wave echoes: a tissue marking device; and a transporter adapted to: convey the probe over the tissue sample in use, the probe and the transporter being adapted such that, in use, information about the tissue sample is collected sufficient to permit a radiologist to identify structures which resemble lymph nodes in the tissue sample; and convey the tissue marking device to locations of (Continued)

interest which correspond to the locations of structures which resemble lymph nodes in the tissue sample.

15 Claims, 26 Drawing Sheets

(51) Int. Cl.
  *A61B 8/08* (2006.01)
  *G01N 29/06* (2006.01)
  *G01N 33/483* (2006.01)
(52) U.S. Cl.
  CPC ..... *G01N 29/0654* (2013.01); *G01N 33/4833* (2013.01); *G01N 2291/0289* (2013.01)
(58) Field of Classification Search
  CPC .... G01N 29/24; G01N 29/02475; A61B 8/08; A61B 8/4209; A61B 8/42; A61B 8/54; G01S 7/52079; G01S 15/8938; G01S 7/52036
  USPC .......................................................... 73/629
  See application file for complete search history.

(56) References Cited

FOREIGN PATENT DOCUMENTS

| | | | |
|---|---|---|---|
| WO | 2020157870 A1 | 8/2020 | |
| WO | WO-2023283734 A1 * | 1/2023 | ............... A61B 8/42 |

* cited by examiner

Status of block according to the "gold standard"/histology

|  | | Contains lymph nodes | Does not contain lymph nodes | |
|---|---|---|---|---|
| Result from screening test/radiology | Positive | a<br>6<br>True positive | b<br>0<br>False positive | ← Row entries for determining positive predictive value |
|  | Negative | c<br>0<br>False negative | d<br>14<br>True negative | ← Row entries for determining negative predictive value |

↑ Column entries for determining sensitivity     ↑ Column entries for determining specificity

- Sample size= 20 blocks

- Histology confirmed 6 blocks with lymph nodes

- Radiologist identified 6 blocks with potential lymph nodes for histology submission

- Sensitivity = [TP / (TP+FN)] x 100% = 100%

- Specificity = [TN / (FP+TN)] x 100% = 100%

- Accuracy = (TN + TP)/ (TN+ TP + FN + FP) = 100%

- Positive Predictive Value = [TP / (TP + FP)] x 100% = 100%

- Negative Predictive Value = [TN / (FN + TN)] x 100% = 100%

FIG. 18

Left mark = histology; Right mark = radiology

|  |  | Column | | | |
|---|---|---|---|---|---|
|  |  | A | B | C | D |
| Row # | 1 | - - | - - | - - | - - |
|  | 2 | - - | + + | + + | - - |
|  | 3 | + + | - - | - - | - - |
|  | 4 | - - | + + | - - | + + |
|  | 5 | - - | + + | - - | - - |

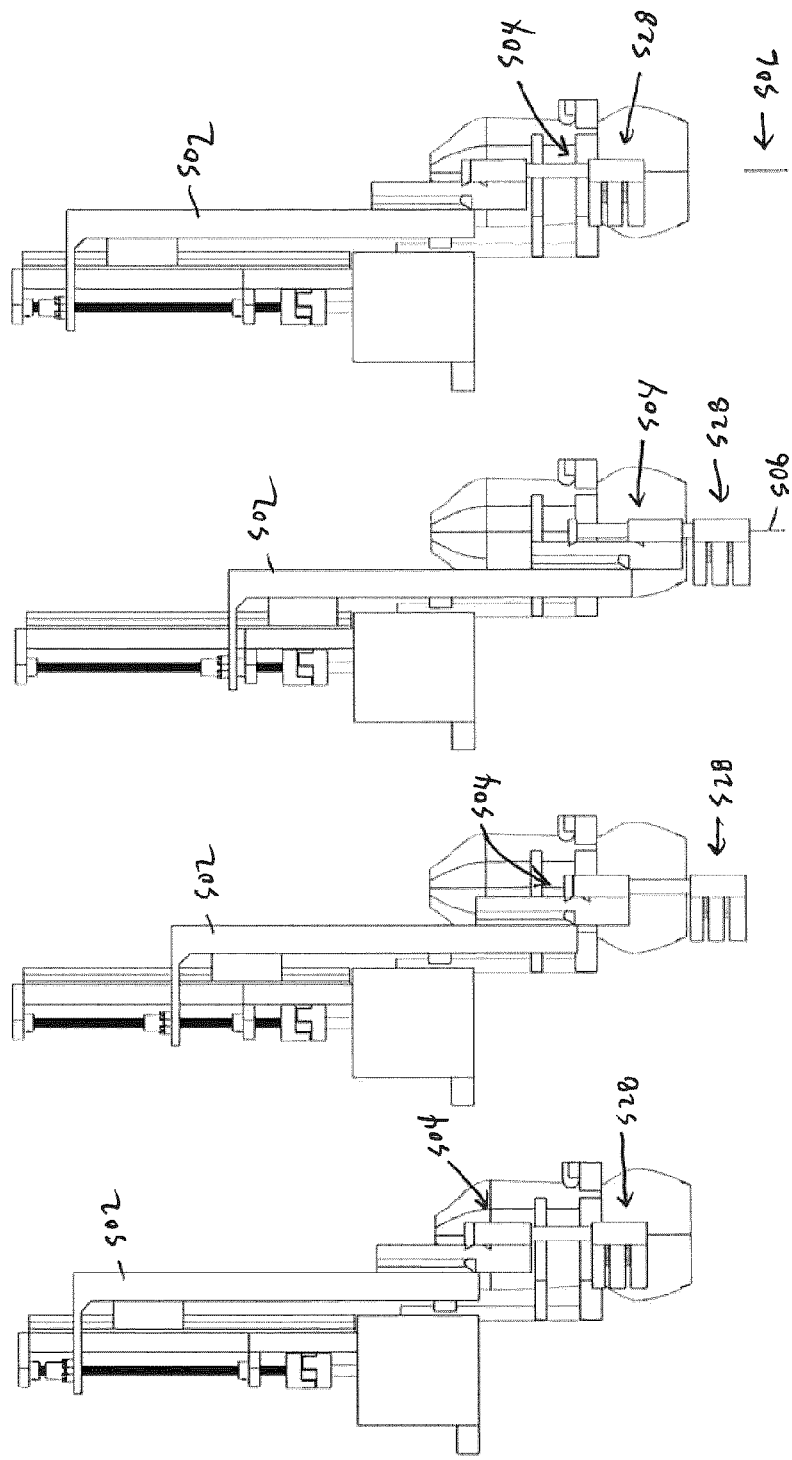

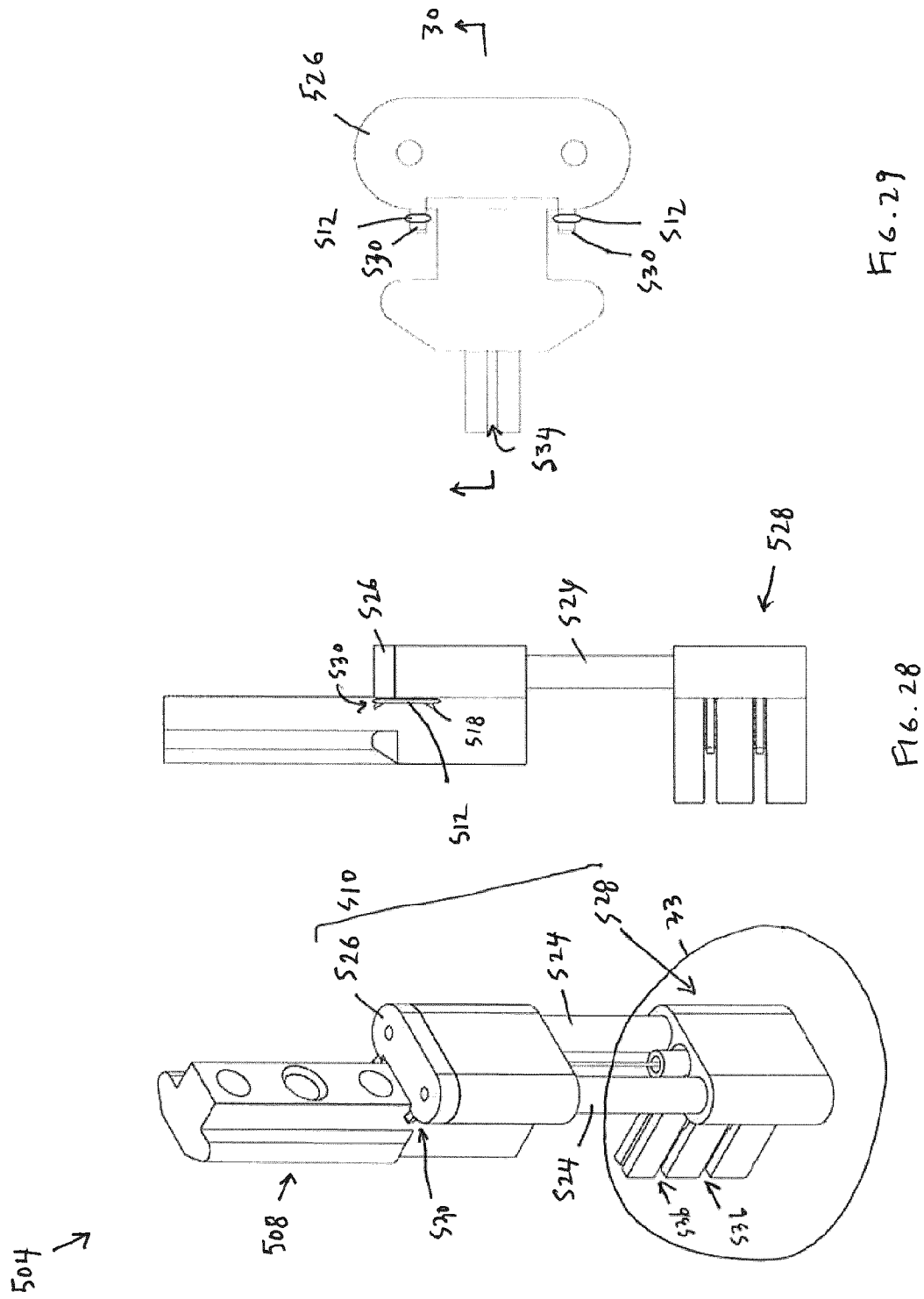

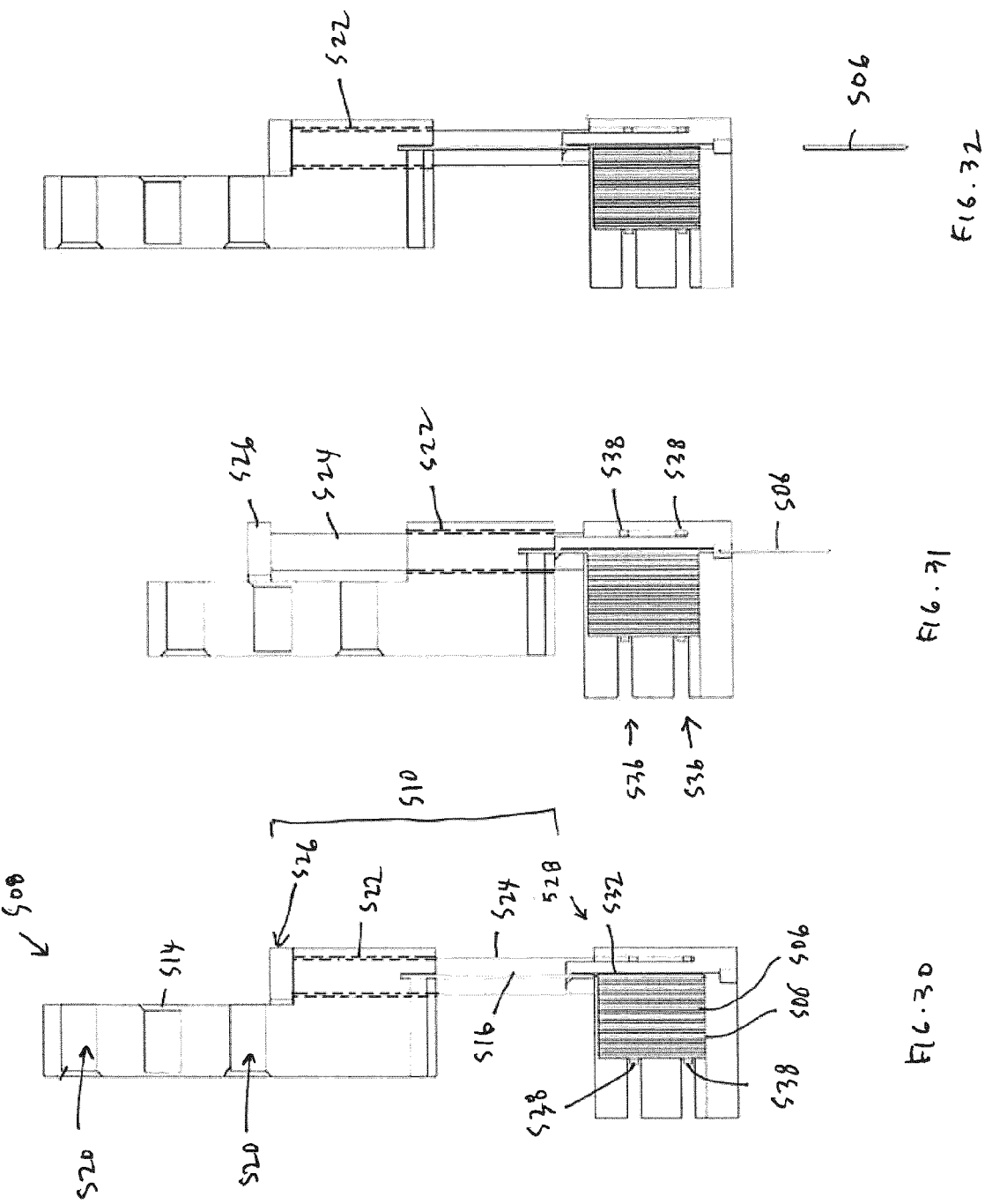

LYMPH NODE LOCATING DEVICE

CROSS-REFERENCE TO RELATED APPLICATIONS

This application claims priority under 35 U.S.C. § 365 to PCT/CA2022/051089 filed on Jul. 13, 2022, entitled "Lymph Node Locating Device," and U.S. provisional application 63/221,172, filed Jul. 13, 2021, entitled "Lymph Node Locating Device." The entirety of the aforementioned applications are incorporated herein by reference.

FIELD

The present invention relates to resected tissue processing in clinical workflow, and more particularly to detection or identification of lymph nodes in surgically resected tissue.

BACKGROUND

Lymph node (LN) analysis, for example lymphadenopathy evaluation, is desired in clinical workflow. LN analysis occurs in assessment of various diseases including, for example, infectious, autoimmune or malignant disease. For example, LN staging is a primary parameter of the internationally adopted TNM classification standard for solid tumor cancers—in the abbreviation TNM, T references an originating tumor, N references lymph nodes, and M references metastasis.

An existing clinical practice for LN searching in a surgically resected tissue sample involves serial slicing of resected tissues that are then stretched and examined for LNs through visual inspection, palpation, and manual dissection (MND)—a procedure generally reserved for pathology residents, pathologists' assistants (PA) and in some instances, staff pathologists.

A mechanical device has been proposed to aid LN detection and extraction. Developed by Omnia Inventa Medical, the LNL300 is a mechanical device that is hand-operated and allows pathology staff to extract LNs from resected tissue specimens.

Briefly, the workflow for this device is described in the following points below:
- The dissector is required to first manually palpate the specimen for any large LNs and remove them from the gross specimen; this is done to prevent double counting of LNs, especially cancer positive LNs, since the mechanics of this device may accidentally slice larger LNs in half
- Following removal of the large palpable LNs, the dissector is required to make several superficial incisions every 0.5-1 cm on both sides of the fatty tissues and then cut these tissues into long strips about 0.5 cm wide (no larger than 1 cm in width)
- Once these strips have been cut, the dissector is required to put these tissues into a large volume of fat dissolving solvents (either acetone, 95% alcohol or Carnoy's acetone) for at least 6 hours or overnight to allow for better cohesion and compression of the tissues when using the device in the subsequent steps
- Once the tissue strips are fixed, components of the device are assembled and up to 250 grams of fatty tissues are packed into a loading chamber, where a crank is then manually turned which then drives a plunger and compresses the tissues down an apparatus with exit points/holes. According to the developers of the LNL300 mechanical device, based on certain "fully saturated porous media" theories and "Terzaghi's principle", the compression of the fat (down the tube containing the exit points) will allow the removal of the fluid present in the interstices of solid fat/tissue particles, thereby allowing successful compression of the specimen into a precisely sized tissue block
- From there, a cutting chamber is attached and subsequently used for the tissue block, where serial sectioning (single cuts) takes place. The tissue slices are then directly placed into a standard tissue cassette
- This process is repeated until all of the tissue has been processed (just 250 g at a time)

SUMMARY OF THE INVENTION

A system for use with a tissue sample forms one aspect of the invention. The system comprising a tray for receiving the tissue sample in use and an apparatus. The apparatus includes:
- a support which receives the tray in use;
- a probe adapted to transmit waves and identify wave echoes;
- a tissue marking device; and
- a transporter adapted to:
  - convey the probe over the tissue sample in use, the probe and the transporter being adapted such that, in use, information about the tissue sample is collected sufficient to permit a radiologist to identify structures which resemble lymph nodes in the tissue sample; and convey the tissue marking device to locations of interest which correspond to the locations of structures which resemble lymph nodes in the tissue sample.

According to another aspect, the probe can be an ultrasound probe and the transporter is adapted to automatically convey the probe to capture a complete ultrasound image of the tissue sample.

According to another aspect, the system can further comprise a computing facility adapted to:
- permit the complete ultrasound image to be viewed on a screen; and
- permit a viewer to make, on the screen and with one or more of a mouse, stylus, keyboard or touchscreen interface, selections, each selection being a structure which resembles a lymph node; and
- generate the locations of interest based upon the selections.

According to another aspect, the transporter can be adapted to automatically convey the tissue marking device to each of the locations of interest and the tissue marking device is adapted to automatically place a mark at each of the locations of interest.

According to another aspect, the transporter system can comprise an X-Y table.

According to another aspect, the tissue marking device can be a pin setter.

A method for use with a tissue sample forms another aspect of the invention. The method comprises:
- immobilizing the sample in a tray;
- automatically conveying a probe adapted to transmit waves and identify wave echoes over the tissue sample to collect information about the tissue sample sufficient to permit a radiologist to identify structures which resemble lymph nodes in the tissue sample;
- identifying locations of interest in the sample using the information, each location of interest corresponding to the location of a structure which has a radiologic resemblance to a lymph node; and automatically marking each of the locations of interest by automatically conveying a marking device thereto.

According to another aspect, the probe can be an ultrasound probe.

According to another aspect, the probe and the marking device can be automatically conveyed by the same apparatus.

According to another aspect, the tray can be removed from the apparatus after the information is collected and placed in the apparatus after the locations of interest have been identified.

According to another aspect, a radiologist can: use a computing facility having a screen to view an ultrasound image of the tissue sample; and make, on the screen and with one or more of a mouse, stylus, keyboard or touchscreen interface, selections, each selection being a structure which resembles a lymph node.

According to another aspect, the computing facility can generate the locations of interest based upon the selections.

According to another aspect, the tray can be placed in the apparatus after the sample is immobilized.

A lymph node locating device forms another aspect of the invention. The device comprises:
 a base;
 a tray coupled to the base, the tray defining a reservoir for holding a resected tissue sample; and
 a gantry actuating at least two degrees of freedom of motion of an ultrasound probe.

In another aspect there is provided a computer implemented lymph node locating method comprising:
 obtaining ultrasound scan data of a resected tissue sample comprising a plurality of image frames captured during acquisition of the ultrasound scan data and a plurality of position coordinates recorded during acquisition of the ultrasound scan data;
 registering each of the plurality of image frames to a unique one of the plurality of position coordinates so that each of the plurality of image frames is registered to a unique position coordinate; and
 selecting at least one image frame showing a lymph node and recording the selected image frame as a lymph node region of interest with its associated unique position coordinate.

In yet another aspect there is provided a lymph node locating system comprising:
 a memory for storing ultrasound scan data of a resected tissue sample comprising a plurality of image frames captured during acquisition of the ultrasound scan data and a plurality of position coordinates recorded during acquisition of the ultrasound scan data; and
 a processor configured to register each of the plurality of image frames to a unique one of the plurality of position coordinates so that each of the plurality of image frames is registered to a unique position coordinate and configured to select at least one image frame showing a lymph node and configured to record the selected image frame as a lymph node region of interest and its associated unique position coordinate.

In further aspects, systems and methods for controlling the device are also provided.

Advantages, features and characteristics of the invention will become evident upon a review of the following detailed description, with reference to the appended drawings, the latter being briefly described hereinafter.

BRIEF DESCRIPTION OF THE DRAWINGS

In the following drawings:

FIG. 10A shows a flow diagram of an example of a complete workflow of locating LNs in a resected tissue sample providing illustrative steps of tissue orientation, tissue scanning and data acquisition, data inspection, LN identification, marking and excision from the resected tissue sample.

FIG. 10B shows a flow diagram of capturing and registering image and location data from an ultrasound scan in the LN locating method shown in FIG. 10A.

FIG. 10C shows a flow diagram of an alternative example of capturing and registering image and location data from an ultrasound scan in the LN locating method shown in FIG. 10A. FIG. 10D shows a flow diagram for image data inspection in the LN locating method shown in FIG. 10A.

FIG. 10E shows a flow diagram for an alternative example of image data inspection in the LN locating method shown in FIG. 10A.

FIG. 10F shows a flow diagram for another alternative example of image data inspection in the LN locating method shown in FIG. 10A.

FIG. 10G shows a flow diagram for tissue marking in the LN locating method shown in FIG. 10A.

FIG. 10H shows a flow diagram for tissue excision in the LN locating method shown in FIG. 10A.

FIG. 17 shows performance parameters of the device and histology. Following cross-correlation of the independent findings from radiology and pathology, the sensitivity (the ability of a test to correctly identify a square/block with LNs), specificity (the ability of the test to correct identify a block without LNs), accuracy (overall agreement between the gold standard [H&E staining] and the test), positive predictive value (the likelihood that the block sent to histology is positive for LNs), and the negative predictive value (the likelihood that the block sent to histology is negative for LNs) were calculated (two-sided P-value of <0.0001 by Fisher's exact test, N=20 blocks).

FIG. 18 shows a grid layout demonstrating the positive and negative blocks independently identified by pathology and radiology. Both findings from radiology and pathology identified 6 blocks that contained LNs, while the other 14 blocks did not contain LNs.

FIG. 23 is a side view of the structure of FIG. 22 in a fully retracted position FIG. 24 is a view similar to FIG. 23 at a firing position FIG. 25 is a view similar to FIG. 23 at a discharged position FIG. 26 is a view similar to FIG. 23 at the fully retracted position FIG. 27 is an enlarged view of the structure of encircled area 27 of FIG. 21;

FIG. 28 is a side view of the structure of FIG. 27

FIG. 29 is a plan view of the structure of FIG. 27

FIG. 30 is a view along section 30-30 of FIG. 29, configured as in FIG. 23

FIG. 31 is a view similar to FIG. 30, configured as in FIG. 25;

FIG. 32 is a view similar to FIG. 30, configured as in FIG. 26,

FIG. 32 is a view along section 31-31 of FIG. 26;

DETAILED DESCRIPTION

Figure 1:
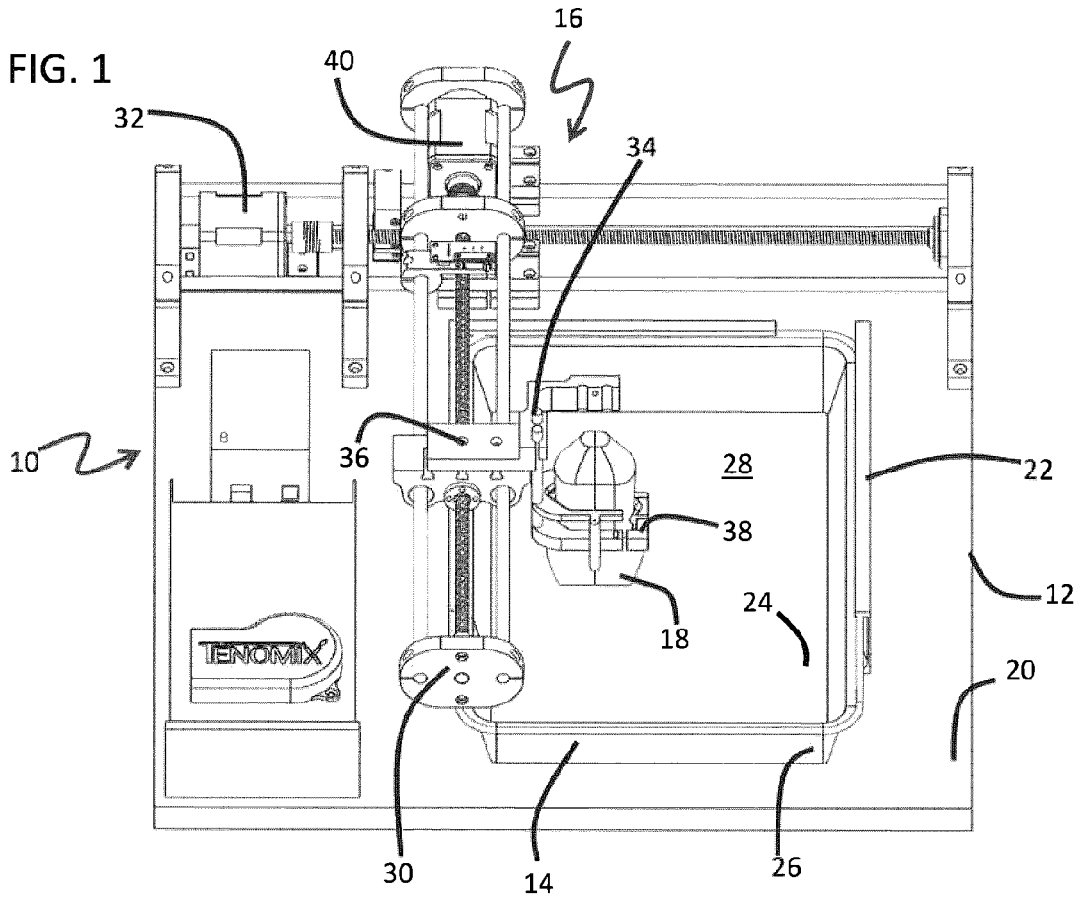
FIG. 1 shows a top-front perspective view of an example of a device for lymph node locating or searching in a resected tissue sample.
Figure 2:
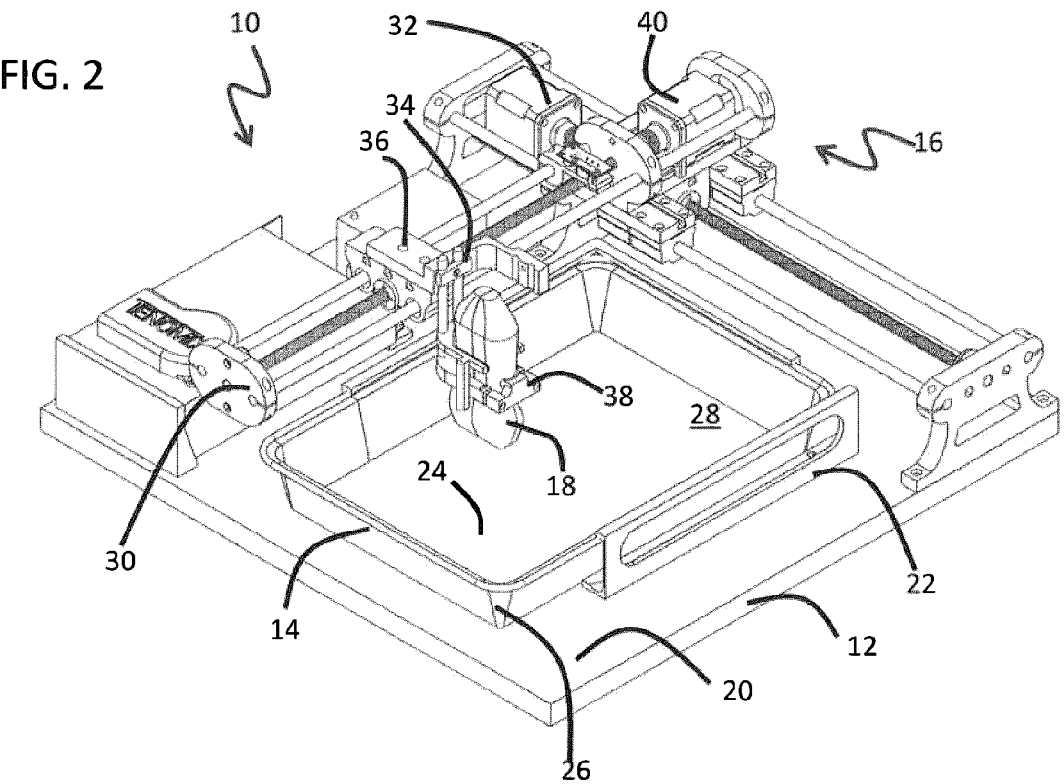
FIG. 2 shows a top-side perspective view of the device shown in FIG. 1.
Figure 3:
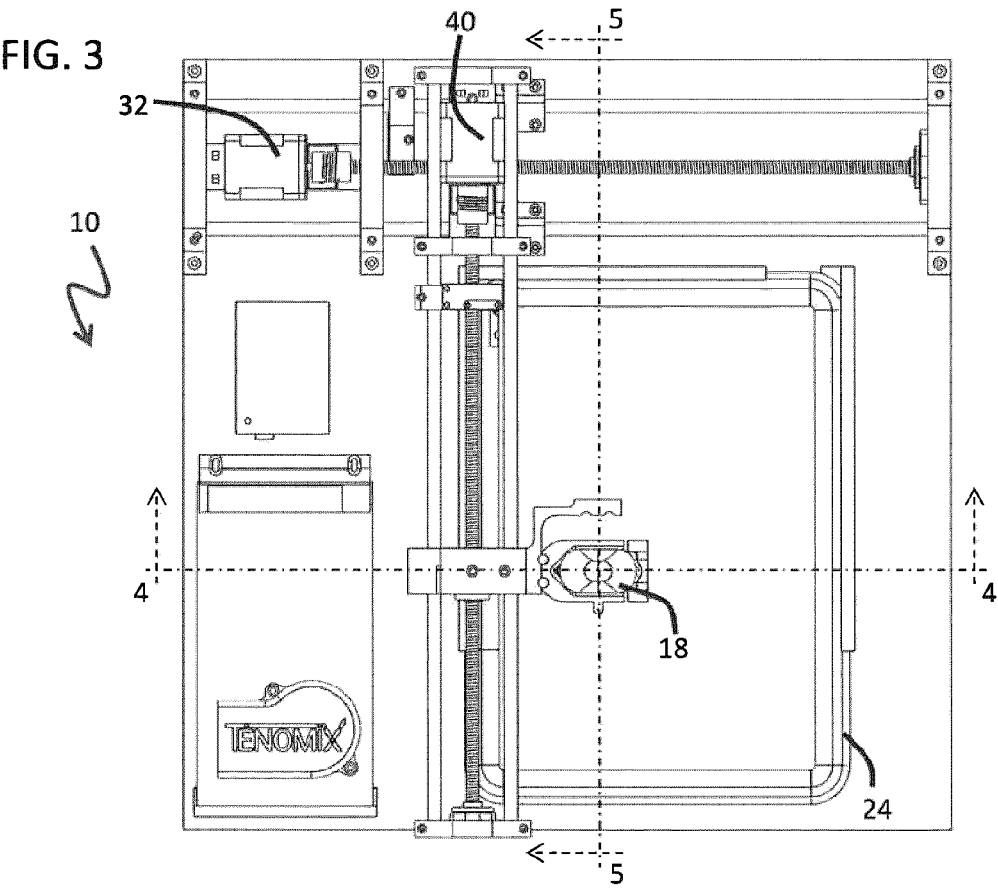
FIG. 3 shows a top elevation view of the device shown in FIG. 1.
Figure 4:
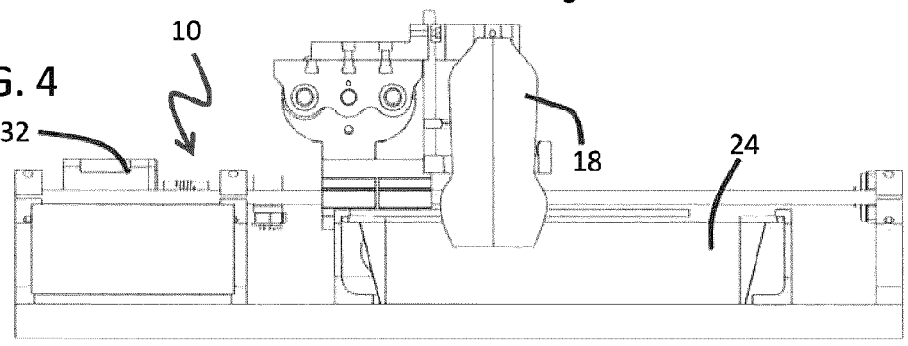
FIG. 4 shows a cross-section view of the device cut along line 4-4 marked in FIG. 3.
Figure 5:
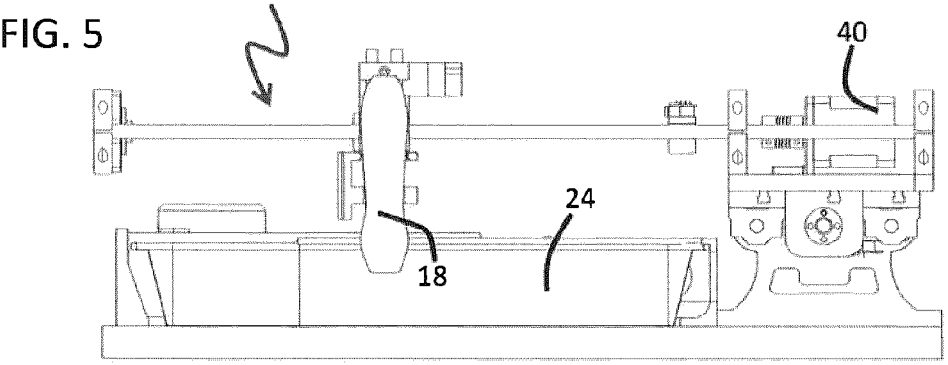
FIG. 5 shows a cross-section view of the device cut along line 5-5 marked in FIG. 3.

Referring to the drawings, a lymph node locating device 10 is shown in FIGS. 1 to 5. The device 10 can be used to detect lymph nodes by imaging a resected tissue sample.

The device 10 comprises a support/base 12, a tray 14 for receiving a resected tissue sample (as shown, for example, in FIGS. 11 and 12) and a transporter/gantry 16 actuating/conveying at least two degrees of freedom of motion of a probe adapted to transmit waves and identify wave echoes, i.e. an ultrasound probe 18.

The base 12 comprises a platform working surface 20 for mounting gantry 16 and supporting tray 14 in a desired orientation relative to gantry 16 and ultrasound probe 18.

The tray 14 is positioned on working surface 20 by reversible coupling to frame 22 that is mounted on the working surface 20. The frame 22 provides a guide for proper positioning of the tray 14 relative to the gantry 16 and ultrasound probe 18. The tray 14 is reversibly coupled to the frame 22 and can be reversibly latched or locked to the frame 22 so as to maintain a fixed desired orientation of the tray 14 within a predetermined work envelope of the gantry 16. The tray defines a mounting surface 24 for receiving and presenting the resected tissue sample for scanning with the ultrasound probe 18. All or part of the mounting surface 24 may optionally be equipped with any conventional chemical or physical support to set or secure the resected tissue sample in a desired orientation.

The mounting surface 24 is bound by a continuous perimeter of sidewalls 26, and the mounting surface 24 and interior surfaces of sidewalls 26 combine to define a reservoir 28 with sufficient volume for receiving and holding the resected tissue sample and an acoustic conducting fluid or medium (as shown, for example, in FIGS. 11 and 12) for acoustically coupling the ultrasound probe 18 to the resected tissue sample. The tray 14 is lined with corkboard and provides an open face opposing the mounting surface 24 so as to provide open access of the reservoir 28 and its contents to the ultrasound probe 18.

The gantry 16 includes a moveable arm 30 coupled to the base, a first linear actuator 32 effecting a first degree of freedom of linear motion of the moveable arm 30 parallel to a first axis. The gantry 16 further includes a moveable gripper 34 coupled to the moveable arm 30. The gripper 34 includes a gripper arm 36 and a harness (or cradle) 38 for holding the ultrasound probe 18, the harness 38 coupled to the gripper arm 36, and the gripper arm 36 coupled to the moveable arm 30. A second linear actuator 40 effects a second degree of freedom of linear motion of the gripper 34 parallel to a second axis. The first linear actuator is mounted to the working surface 20 of the base 12, while the second linear actuator 40 is mounted to the moveable arm 30. The linear motion of the moveable arm 30 is perpendicular to the linear motion of the moveable gripper 34 and together combine to provide a Cartesian coordinate sweep of the tray 24 and its contents.

Figure 6:
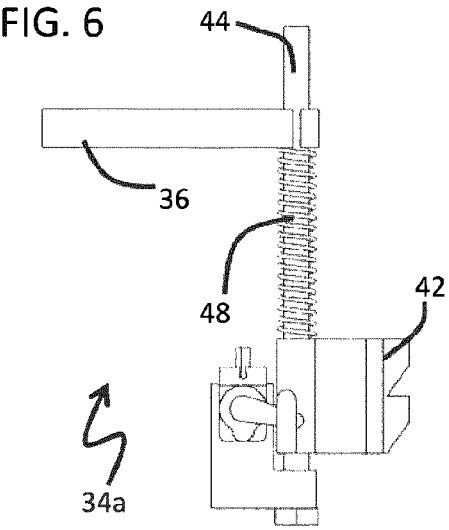
FIG. 6 shows a front view of a marking end effector that can be incorporated in the device shown in FIG. 1.
Figure 8:
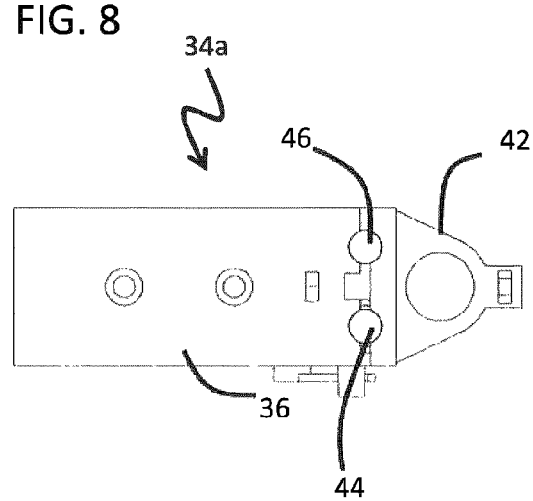
FIG. 8 shows a top elevational view of the marking end effector shown in FIG. 6.
Figure 7:
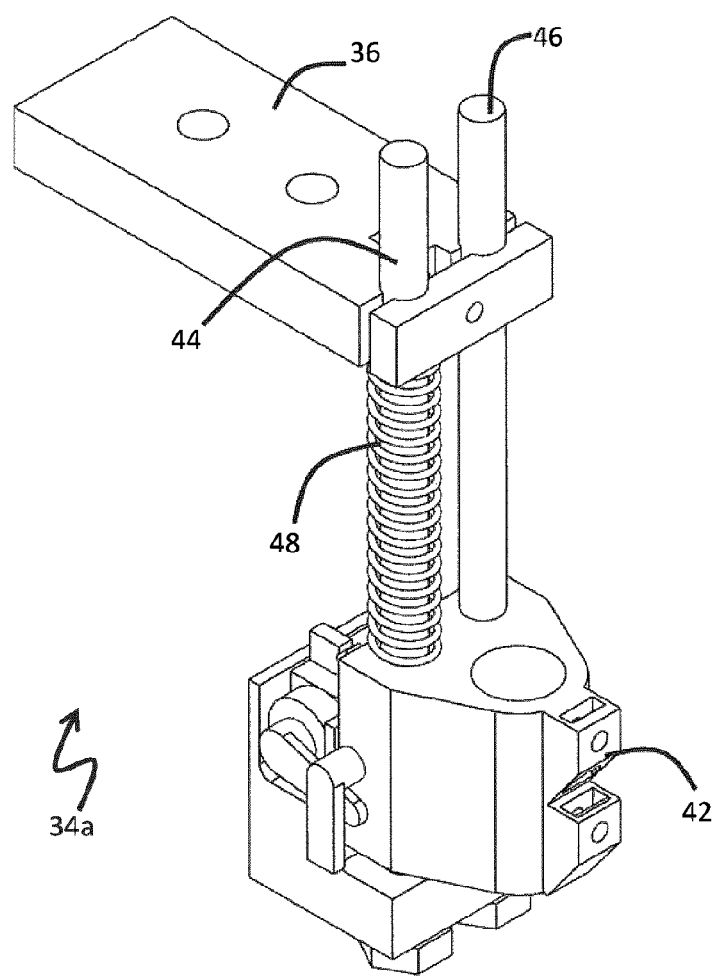
FIG. 7 shows a perspective view of the marking end effector shown in FIG. 6.

FIGS. 6 to 8 show a first variant gripper 34a for holding a marking end effector for placing a visible indicator at an LN location identified within the resected tissue sample. The first variant gripper 34a includes a gripper arm 36 and a clamp 42 for securing the marking end effector, the clamp 42 coupled to the gripper arm 36, and the gripper arm 36 coupled to the moveable arm 30. The clamp 42 is connected two a first rod 44 and a second rod 46, and both first and second rods are slidably coupled to the gripper arm 36. A resilient member 48 mounted to the first rod 44 biases the clamp 42 to a first position relative to the gripper arm, while a third linear actuator (not shown) controlling linear motion of the second rod 46 relative to the gripper arm 36 actuates motion of the clamp in a linear direction opposing the biasing force direction of the resilient member 48. The first variant gripper 34a may optionally replace gripper 34 during marking operation, or the clamp 42 holding the marking end effector may optionally be positioned adjacent to harness 38 with the clamp and the harness both coupled to the gripper arm 36.

The marking end effector can be a conventional tissue marking pen, or a pin gun that can make a marking or eject a pin into a point of interest, both of which are used in pathology laboratories for many dissection procedures. The gantry articulates the marker tip or tip of the pin gun to the XY coordinate of all identified LNs and marks their surface in a sample for easier extraction by a dissector.

A further variant gripper for holding a dissection, excision or extraction tool (not shown) may also optionally be installed to provide computer directed extraction of cores or blocks from the resected tissue sample, with each core or block containing an identified LN.

Figure 9:
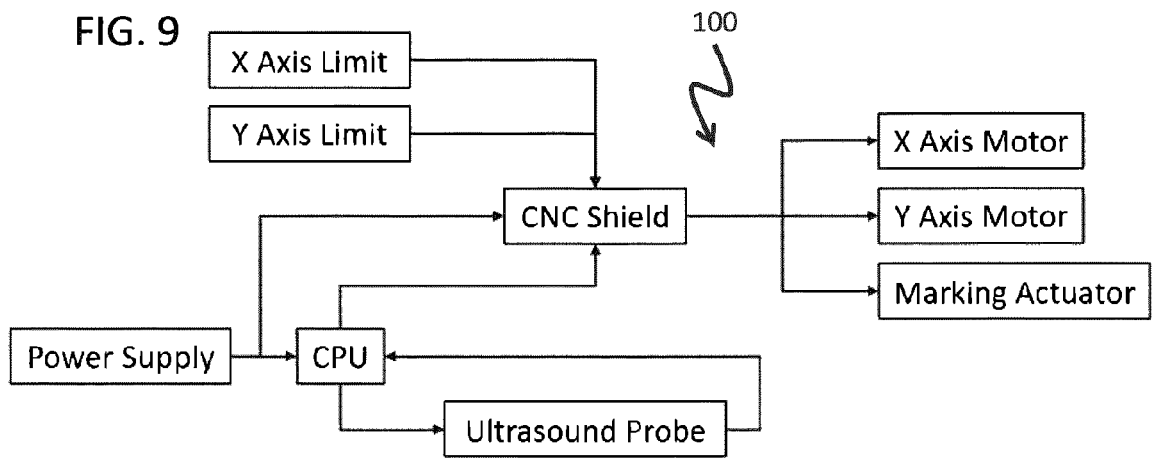
FIG. 9 shows a block diagram map of an example of a LN locating system.

FIG. 9 shows a block diagram schematic representation of a lymph node locating system 100. The system 100 includes a power supply, a main processor or CPU, a CNC Shield which includes a microcontroller or microprocessor, limit switches, and a plurality of motorized linear actuators disposed in a gantry to provide Cartesian coordinate motion to an ultrasound transducer coupled to the gantry. The power supply converts AC 120V to a usable DC Voltage for the CNC Shield and CPU, for example DC 24V for input to CNC Shield and DC 9V to CPU. The CPU powers, adjusts and reads the ultrasound transducer scans, generates and sends movement or navigation commands to the CNC Shield, and serves as a terminal for lymph node identification. The limit switches allow the linear actuators to reset movable components of the gantry to a home or origin reference position and avoid crashes in the event of missed steps. The CNC Shield interprets commands from the CPU and limit switches and converts movement instructions from G-code for interpretation by motor drivers and connects power to the drivers, for example DC 24V. The X axis motor and Y axis motor are examples of motorized linear actuators that drive respective lead screws which in turn translate the scanning, marking and/or excision tools to a desired position or a desired set of positions relative to the resected tissue sample. The marking actuator is a low torque actuator which imparts force on the marking head of the marking tool to place physical indications of regions for dissection (containing LNs).

Figure 10:
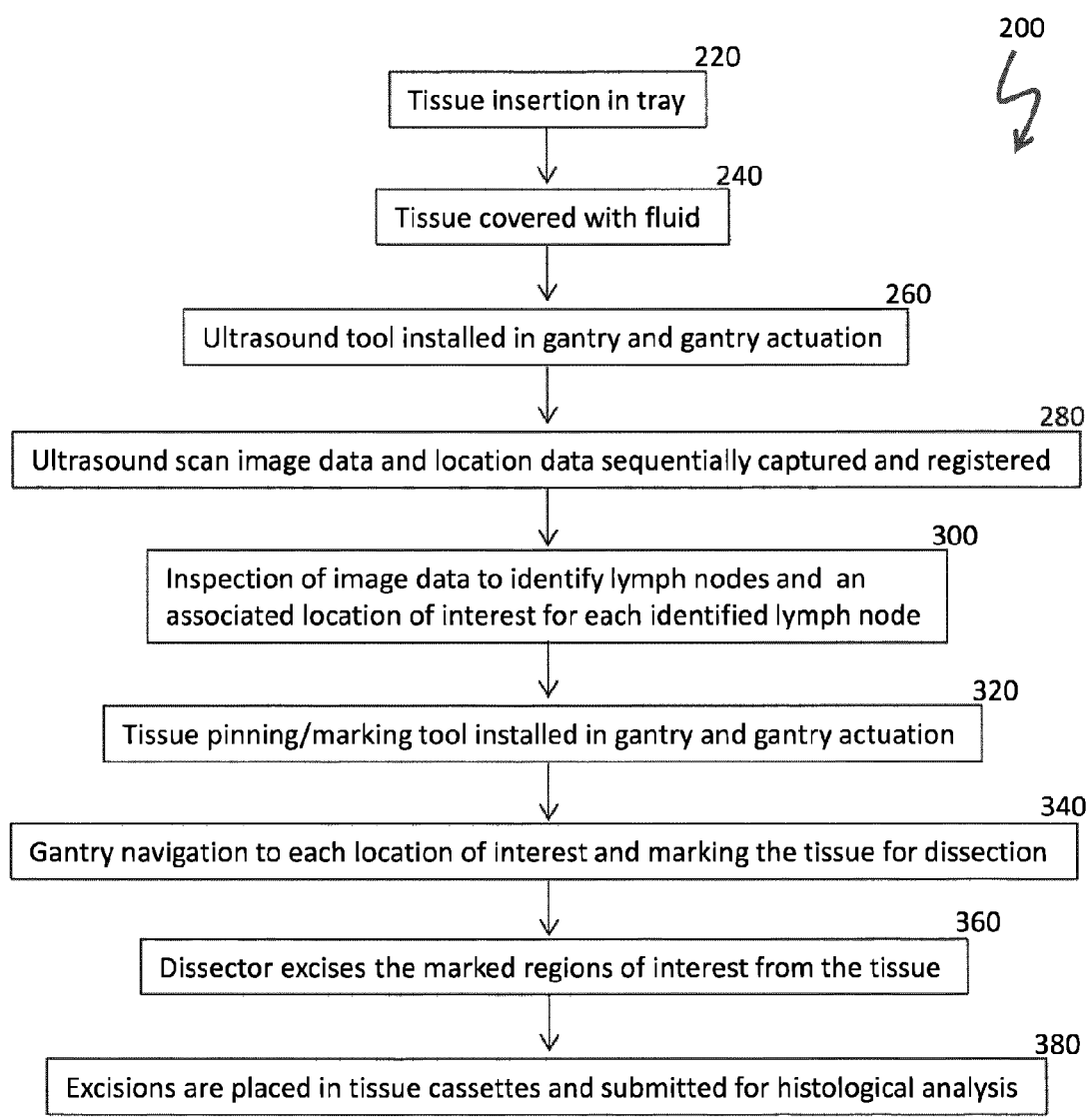
FIG. 10 shows flow charts of LN locating methods.
Figure 10:
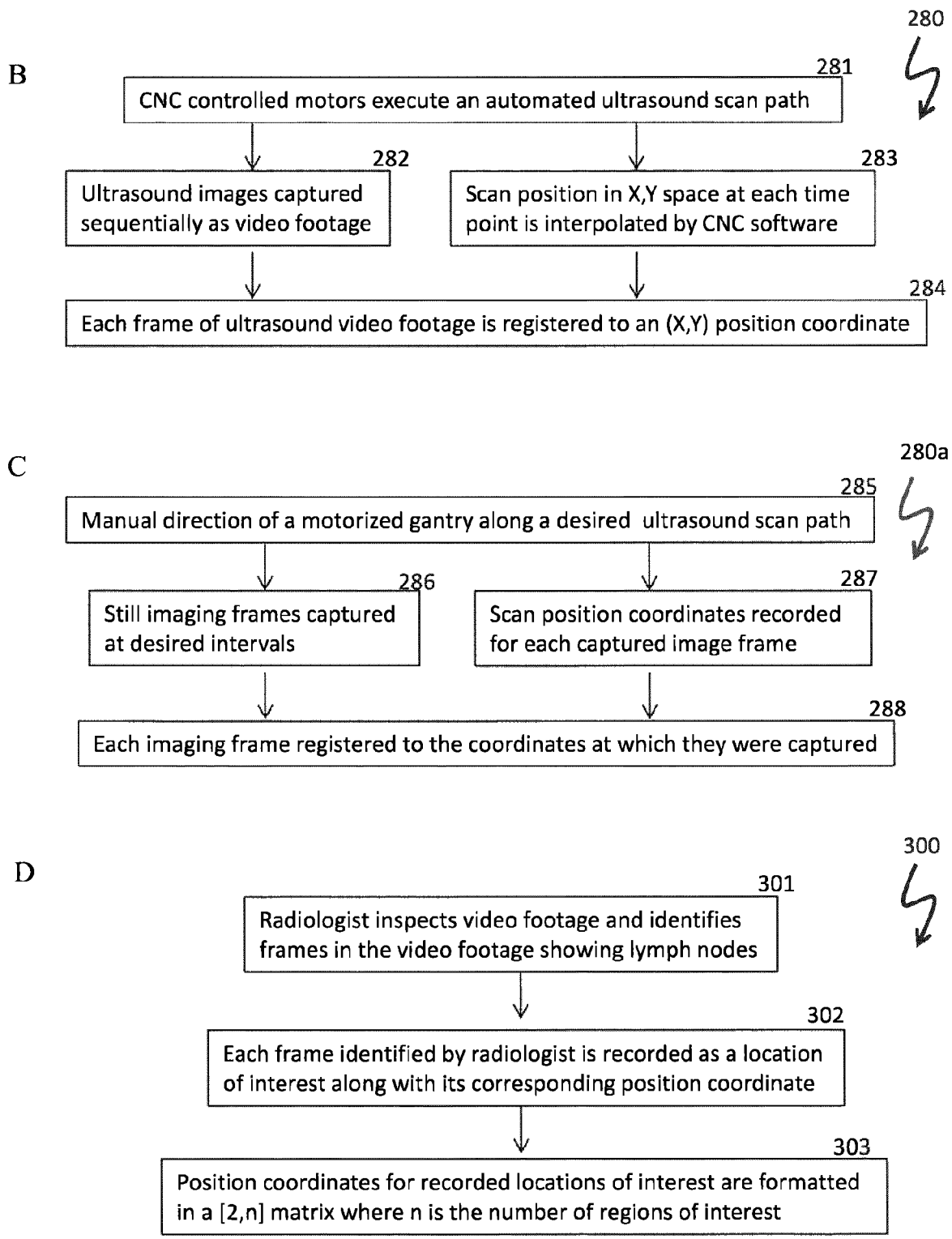
Figure 10:
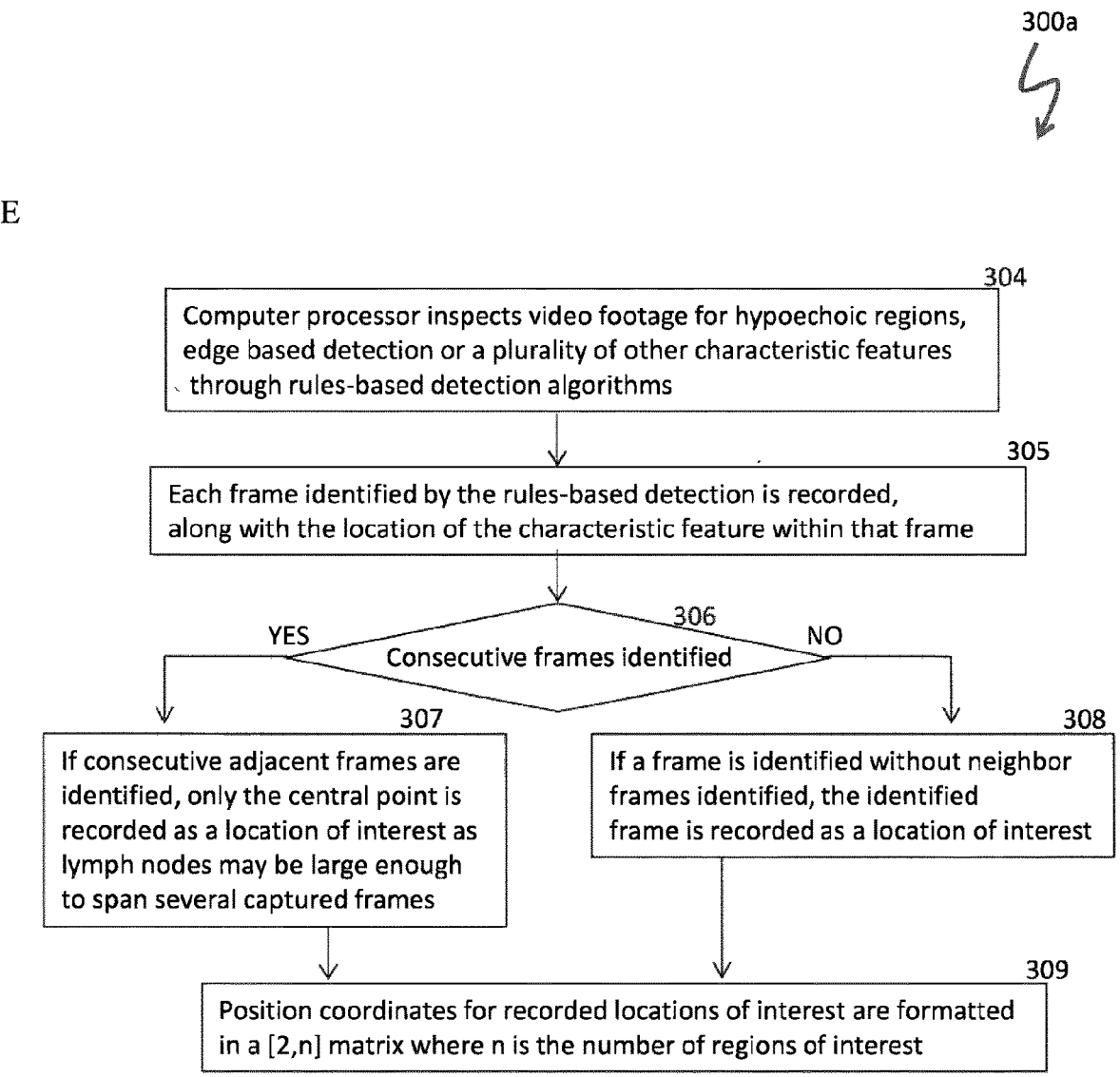
Figure 10:
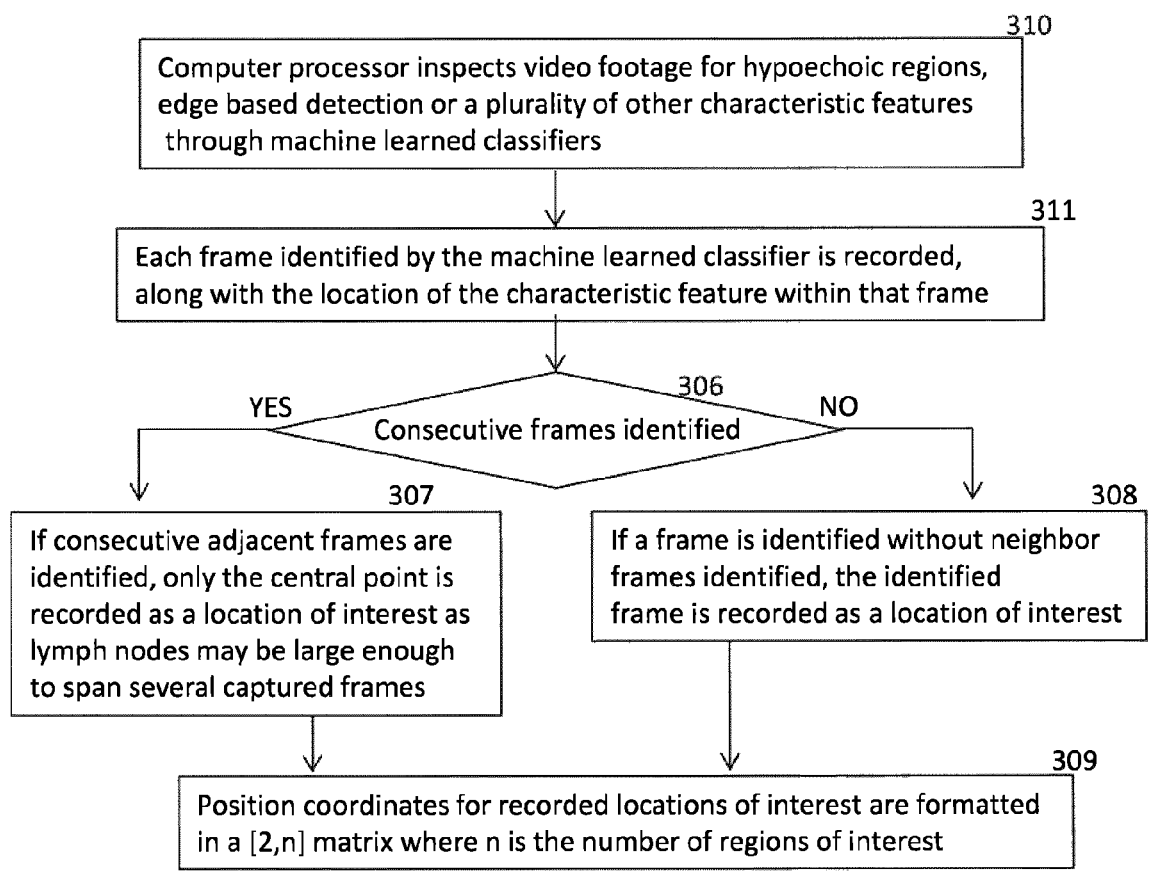
Figure 10:
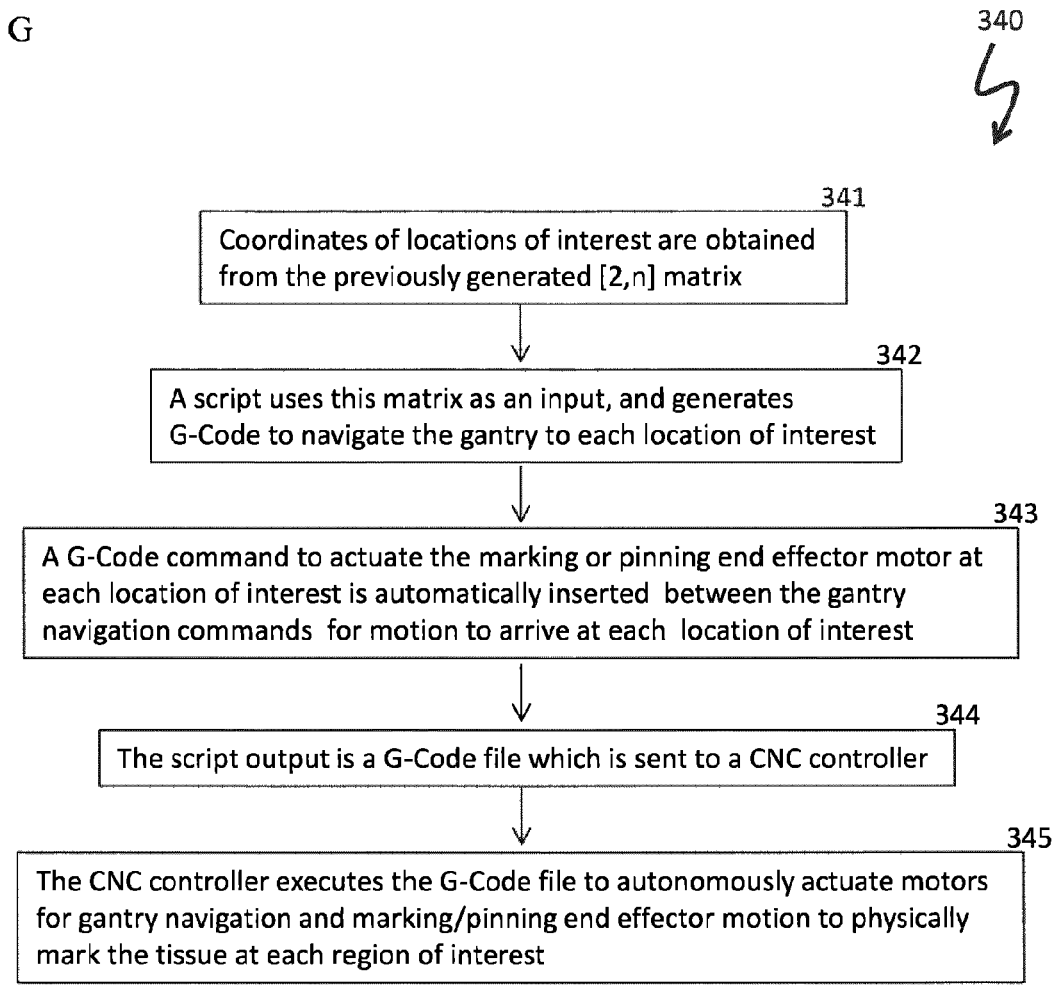
Figure 10:
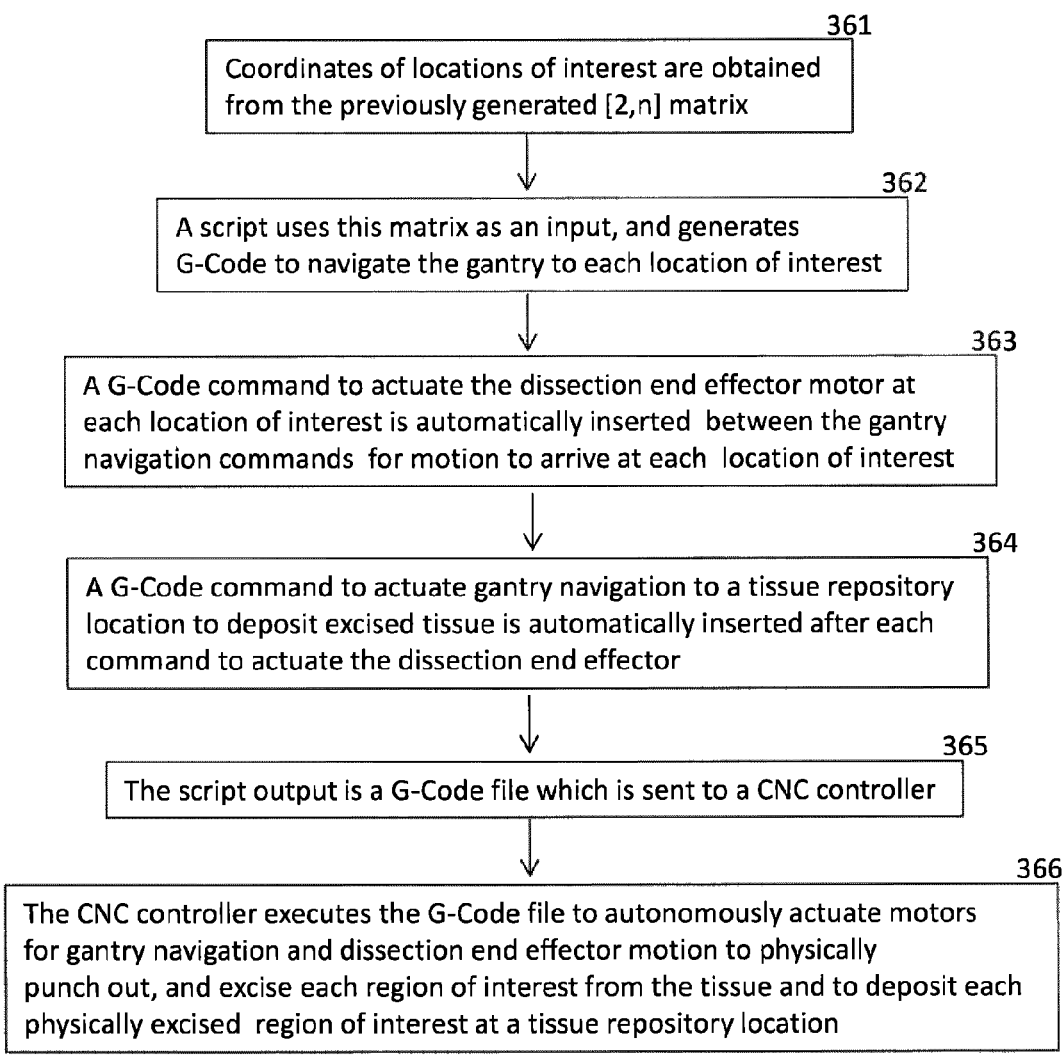

FIG. 10A shows an example of a computer implemented lymph node locating method 200. The method 200 comprises inserting 220 a resected tissue sample in a tray and covering 240 the tissue sample with a sufficient amount of acoustic conducting fluid to provide acoustic coupling between the tissue sample and an ultrasound probe.

A gantry with the ultrasound probe installed is actuated 260 for Cartesian coordinate motion of the ultrasound probe while in physical contact with the acoustic conducting fluid to scan the tissue sample for ultrasound scan data acquisition. Both image data and location data are acquired or captured 280 from the ultrasound scan and the captured image data is registered 280 to its corresponding location data. The captured image data is inspected to identify 300 regions of interest containing lymph nodes to select a subset of image frames from the set of captured image data, and a corresponding location of interest is outputted 300 for each identified lymph node region of interest. The gantry with a marker or pin gun installed is actuated 320 for Cartesian coordinate motion of the marker or pin gun. Directed by the Cartesian position coordinates for each of the one or more locations of interest outputted in step 300, the gantry is navigated 340 to position the marker or pin gun at each location of interest, and the marker or pin gun is actuated to mark 340 each location of interest. Guided by the marking of step 340, a dissector excises 360 cores or blocks from the tissue sample at the marked locations of interest. Each physically excised region of interest is placed 380 in a tissue cassette coded to identify position of the excision, and each tissue cassette is submitted 380 for histological lymph node analysis. The term location of interest is related to but not the same as the term region of interest, as a region of interest is a circumscribed area or volume designated in a 2D or 3D image while a location of interest includes position data for referencing either the corresponding region of interest or one or more points of interest within the corresponding region of interest. If dissection of the resected tissue sample is performed, then the region of interest designated in the image corresponds to an excised core or block from the resected tissue sample, so that an image processing region of interest correlates to a physically excised region of interest.

FIG. 10B shows an example of capturing and registering 280 image and location data from an ultrasound scan. The image and location data capture and registration 280 includes automated control of a motorized gantry holding an ultrasound transducer by a CNC controller, with the CNC controller executing 281 commands to navigate the gantry along a predetermined ultrasound scan path. During progression of the gantry and ultrasound transducer through the ultrasound scan path, ultrasound image data is captured 282 as video footage in combination with CNC software directed recording and interpolation 283 of position coordinates at each time point. The captured image data is registered 284 to the recorded position data so that each frame of ultrasound video footage is registered to a unique position coordinate.

FIG. 10C shows an alternative example of capturing and registering 280a image and location data from an ultrasound scan. This alternative example of image and location data capture and registration 280a includes manual directed control 285 of a motorized gantry holding an ultrasound transducer, to navigate 285 the gantry along a desired ultrasound scan path. During progression of the gantry and ultrasound transducer through the ultrasound scan path, ultrasound still image frames are captured 286 optionally with a time stamp in combination with recording 287 of position data for each captured image frame optionally with a time stamp, for example, as provided by position encoders or sensors coupled to the gantry. The captured image data is registered 288 to the recorded position data so that each captured image frame is registered to a unique position coordinate.

FIG. 10D shows an example of image data inspection 300 to identify image fames that show a lymph node region of interest from the image data captured in step 280. The image data inspection 300 includes a radiologist inspecting 301 the captured video footage and identifying 301 or selecting frames that show lymph nodes. Each identified or selected frame is recorded 302 with its corresponding position coordinate. A set of position coordinates with each member of the set corresponding to a unique identified frame is formatted 303 in a matrix for output to the gantry navigation controller.

FIG. 10E shows an alternative example image data inspection 300a to identify image fames that show a lymph node region of interest from the image data captured in step 280. This alternative example of image data inspection 300a includes a computer processor inspecting 304 the captured video footage and automatically identifying 304 or selecting frames that show lymph nodes based on rules-based detection algorithms. Each identified or selected frame is recorded 305 with its corresponding position coordinate. A set of position coordinates with each member of the set corresponding to a unique identified frame is formatted 309 in a matrix for output to the gantry navigation controller. The computer processor is configured to accommodate a possibility of a single large lymph node that is shown in multiple consecutive adjacent or neighboring frames. The computer processor is configured to determine 306 whether consecutive adjacent frames are identified. If consecutive adjacent frames are identified, only the central frame is recorded 307 as a location of interest as lymph nodes may be large enough to span several captured frames. Otherwise, if a frame is identified without neighbor frames identified, the identified frame is recorded 308 as a location of interest.

FIG. 10F shows another alternative example image data inspection 300b to identify image fames that show a lymph node region of interest from the image data captured in step 280. This alternative example of image data inspection 300b includes a computer processor executed machine learned classifier inspecting 310 the captured video footage and automatically identifying 310 or selecting frames that show lymph nodes. Each identified or selected frame is recorded 311 with its corresponding position coordinate. A set of position coordinates with each member of the set corresponding to a unique identified frame is formatted 309 in a matrix for output to the gantry navigation controller. The computer processor is configured to accommodate a possibility of a single large lymph node that is shown in multiple consecutive adjacent or neighboring frames. The computer processor is configured to determine 306 whether consecutive adjacent frames are identified. If consecutive adjacent frames are identified, only the central frame is recorded 307 as a location of interest as lymph nodes may be large enough to span several captured frames. Otherwise, if a frame is identified without neighbor frames identified, the identified frame is recorded 308 as a location of interest.

The examples of image data inspection (radiologist in step 300, rules-based image processing software in alternative step 300a, and machine learned classifier in alternative step 300b) shown in FIGS. 10D, 10E and 10F are described for inspection of image data captured in step 280, but each example can be readily adapted to accommodate image data captured in alternative example step 280a or other alternatives for data acquisition and registration of image data and location data.

FIG. 10G shows an example of automated tissue marking 340 to visually mark lymph node regions of interest within the resected tissue sample. The tissue marking 340 includes a computer processor configured to generate computer executable code for gantry navigation to each identified location of interest by retrieving 341 position coordinates of identified locations of interest from a computer memory component and inputting 342 the retrieved position coordinates within the computer executable code. The computer processor is also configured to insert 343 a command for actuating marking tool motion to achieve physical marking after a navigation command directing gantry motion to a location of interest and before a subsequent navigation command directing gantry motion to a subsequent location of interest. The generated computer executable code is sent 344 to a controller, and the controller executes 345 the generated code to actuate motorized gantry motion and motorized marking tool motion to physically mark the resected tissue sample at each lymph node region of interest.

FIG. 10H shows an example of automated tissue excision 360 to physically excise lymph node regions of interest from the resected tissue sample. The tissue excision 360 can replace the tissue marking 340 (i.e., tissue marking is not done) with step 320 modified for actuated gantry motion of a dissection tool instead of a marking tool. The tissue excision 360 includes a computer processor configured to generate computer executable code for gantry navigation to each identified location of interest by retrieving 361 position coordinates of identified locations of interest from a computer memory component and inputting 362 the retrieved position coordinates within the computer executable code. The computer processor is also configured to insert 363 a command for actuating dissection tool motion to excise a core or block containing a lymph node region of interest after a navigation command directing gantry motion to a location of interest and before a subsequent navigation command directing gantry motion to a subsequent location of interest. The computer processor is also configured to insert 364 a command to actuate gantry navigation to a tissue repository location to deposit excised tissue after each command to actuate the dissection tool at a current location of interest and before the navigation command to proceed to the subsequent location of interest. The generated computer executable code is sent 365 to a controller, and the controller executes 366 the generated code to actuate motorized gantry motion and motorized dissection tool motion to physically excise a lymph node region of interest from the resected tissue sample and to deposit each physically excised region of interest at the tissue repository location.

The device, system and method for locating LN in resected tissue have been validated by experimental testing. Experimental testing results demonstrate the ability of the device, system and method to identify or detect one or more LN locations within a resected tissue sample. The following experimental examples are for illustration purposes only and are not intended to be a limiting description.

In Experimental Example 1, a novel LN locating device and system is evaluated for ability to accurately point out which tissue blocks/squares warrant histopathological analysis, and which do not. In the clinical context, the PA is instructed to find all of the LNs in a resected specimen and oftentimes, when patients have been pre-treated with neo-adjuvant chemotherapy, finding LNs become increasingly difficult. When less than 12 LNs are found in these cases, PAs have to submit additional sections of mesenteric tissues for further tissue processing.

Due to these reasons, we wanted to replicate this clinical scenario in our experiments, where the dissector can accurately submit specific tissue regions (that fit within a 2 by 2 cm tissue cassette), identified by our automated device, for further histology processing. To achieve this, Experimental Example 1 involved the following requirements:
  Obtaining mesenteric adipose tissues from pigs
  Keeping the tissue specimen in a fixed position/orientation Creating a 2 by 2 cm grid across the entire specimen Imaging the specimen with a fixed scanning profile, using ultrasound, and recording the videos Once the scan was completed, each 2 by 2 cm tissue square was placed into a tissue cassette and submitted for further histopathology processing and H&E staining The recorded ultrasound videos were submitted to the radiologist for examination and identification of suspected LNs The findings from the radiologist were then compared to the findings from histology (the 'ground truth'), and downstream analyses were conducted to determine the performance of the device in identifying tissue squares that contained or did not contain LNs.

The materials and methods are described below.

Materials and Methods

Tissue Collection:

Using a porcine animal model for our proof-of-concept experiments, gastrointestinal organs from 3 pigs (including the stomach and large intestines) were generously donated by a local butcher shop, Mount Brydges Abattoir (Mount Brydges, ON, Canada), under the approval of the Ontario Ministry of Agriculture, Food and Rural Affairs. Once the specimens were obtained and fixed in 10% formalin for 24 hours, a pathologist carefully excised the LN-containing mesenteric adipose tissues and the specimen was then immediately prepared for our device.

Figure 11:
FIG. 11 shows an example of embedding a resected tissue specimen. The resected mesenteric tissues (containing LNs) were embedded between 2 layers of agarose. This ensured that the specimen was in a fixed position/orientation during the ultrasound scan.

Fixed Positioning of the Specimen:

In order to maintain the orientation of the tissue during the ultrasound scan, the specimen was encased in 1% agarose gel. Briefly, a layer of agarose (1%; 5 grams of Agarose A in 500 mL of distilled water) was first created to coat the bottom surface of an aluminum tray and the tissue specimen was then placed on top. Once placed, another layer of agarose was gently poured on top of the tissue specimen to encase it (FIG. 11). Agarose embedding is an option for setting tissue orientation, but neither agarose nor any embedding is necessary for maintaining tissue orientation; for example, aluminum dissecting trays containing a layer of paraffin wax provide for the tissue specimen to be physically pinned directly to the paraffin layer of the tray using dissection pins. As further examples, a tray may be equipped with any custom guides, clips, clamps, brackets, bands, and the like that can maintain the tissue in a fixed orientation/position while in the tray.

Water Bath:

Once the specimen was encased in the agarose gel, water was then carefully poured into the tray until the tip of the ultrasound probe was slightly submerged under water. This was done because the use of water and gel can help provide the best acoustic features for ultrasound: a high transmission coefficient and good acoustic coupling [60]. The use of water in our experimental setup also does not require the ultrasound probe to make direct contact with the tissue specimen and thus removes the need for Z axis actuation, which reduces technical barriers to implementation.

Figure 12:
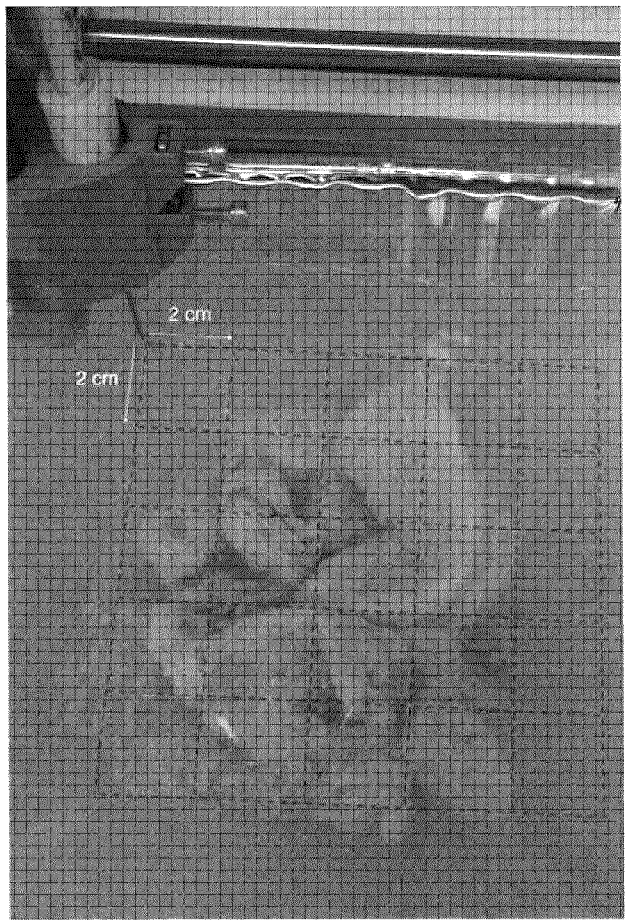
FIG. 12 shows an example of a specimen grid system. A 2 by 2 cm grid system (25 squares in total, with 20 squares containing the tissue of interest) was created to help with post-tissue processing following the completion of the ultrasound scan.

Grid System:

In pathology, standard tissue cassettes are measured at 3×2.5×0.4 cm and it is recommended that tissue specimens should not be cut larger than 2.5×2.0×0.4 cm, otherwise overfilling the cassette with the specimen could lead to improper tissue processing and subsequently, poor quality paraffin-embedded blocks [61,62]. As such, to make post-tissue processing possible after the scan, we constructed a 2 by 2 cm grid (25 squares in total, with 20 squares containing the tissue of interest) that mapped across the entire specimen (FIG. 12).

Although the grid was directly engraved on top of the agarose gel in this experiment, many alternatives are contemplated including, for example, either a physical grid system that is laid out on top or below the specimen, building fiducial markers directly into the frame of the tray, or a grid laser illumination system (with or without the use of machine vision). Furthermore, a grid is not critical and the LN locating device, system or method can operate in absence of a grid.

Figure 13:
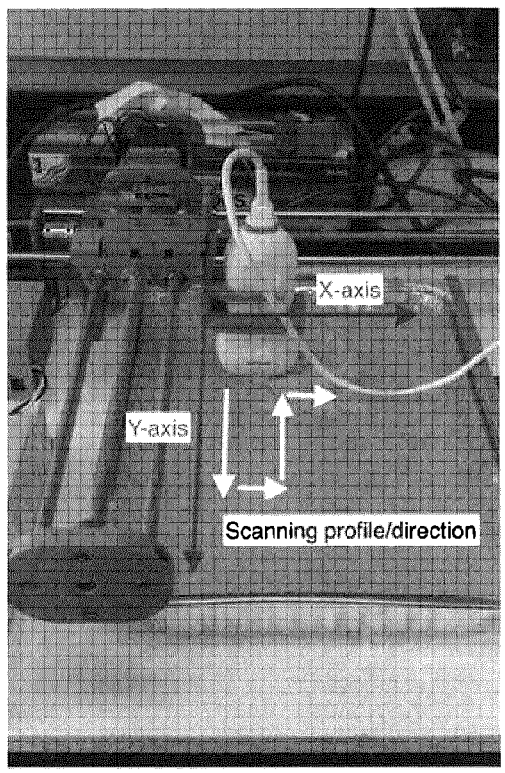
FIG. 13 shows a scanning profile of a cartesian robot implementation of the device 10. The moveable arm and moveable gripper of the cartesian robot were programmed to conduct specific sweeping motions at a travelling speed of 200 mm/s. The homing coordinates of the cartesian robot was at (0,0) and once the scan began, the moveable gripper would travel 130 mm in the Y-direction (towards the operator), a 20 mm shift of the moveable arm in the X direction, followed by the moveable gripper travelling 130 mm in the opposite Y-direction (away from the operator) and this sweeping pattern would continue until the entire tissue is scanned.

Ultrasound Scanning Profile:

Based on the 2 by 2 cm grid described above, a 20-square grid was constructed for the specimen using G-Code, a software programming language for the CNC machine, and the arm of the cartesian robot was programmed to conduct specific sweeping motions at a travelling speed of 200 mm/min (although, up to 720 mm/min would be theoretically appropriate). The home coordinates of the cartesian robot was at global and relative (0,0). Once the scan began, the arm would travel 130 mm in the Y-direction (towards the operator), a 20 mm shift in the X direction, 130 mm in the opposite Y-direction (away from the operator) and this sweeping pattern would continue until the entire tissue is scanned (FIG. 13). Based on the travel speed and the size of the specimen, the scan completed in 3 minutes and 51 seconds. In alternative implementations, the arm speed can be optimized to allow for quicker scans (or slower, depending on the complexity of the specimen and the needs of the end-user). Note the completely parametric design of this robot. Any (practical) scan region could be accommodated if a clinic had larger sample volume requirements by adding longer lead screws and linear bearings to the system to accommodate bigger trays. This could be feasibly scaled to the size of an entire grossing bench if desired. As well, it is important to note that multiple specimens could also be scanned at the same time if desired. Although 1 ultrasound probe orientation was used in this experiment (parallel with the X-Axis), the device includes a 90-degree (rotational) probe mount that allows the capture of both X and Y planes, which would help cross-correlate potential targets and retain the targets that are found in both orientations—this is akin to the sonographer acquiring images of the structure of interest in two orthogonal planes in clinical practice. All scans were conducted with the Lumify L12-4 linear array transducer probe (Philips, USA), 4-12 MHZ, and the videos were recorded on the Lumify ultrasound software application. Of note, these scans can be conducted using commercially available ultrasound probes, for example commercially available linear ultrasound probes which can capture images in the 8-25 MHZ range at greater than 20 frames per second.

Figure 14:
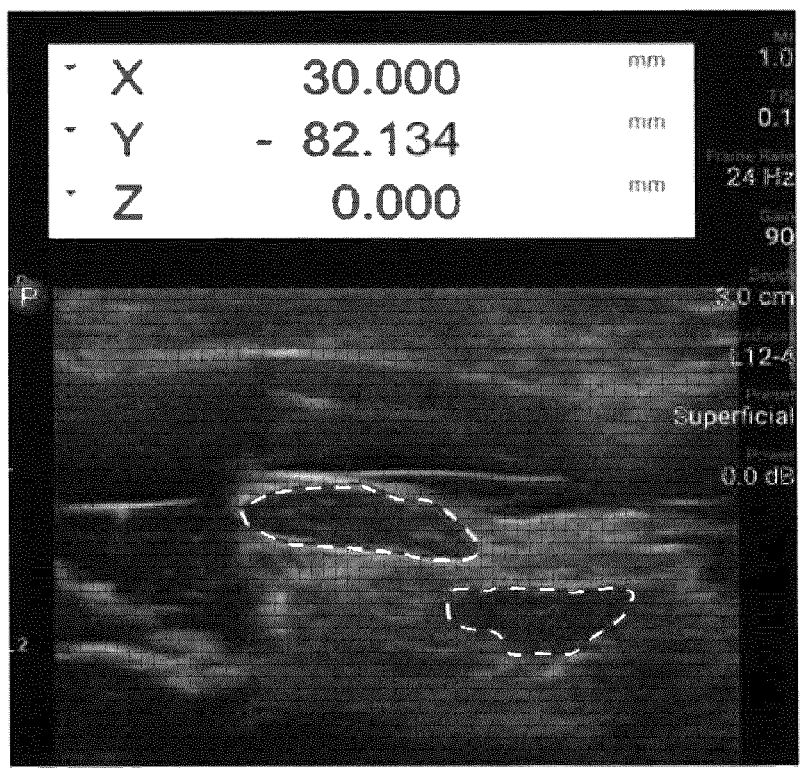
FIG. 14 shows radiography findings and determination of lymph nodes. The recorded ultrasound scans were sent to a radiologist, who was instructed to identify LNs based on their shape and echogenicity (compared with that of the surrounding fatty tissues), and then screenshot and mark the LNs for downstream data analyses. In this image, 2 LNs can be observed with distinct hypoechoic appearances at a specific coordinate in the grid system.
Figure 15:
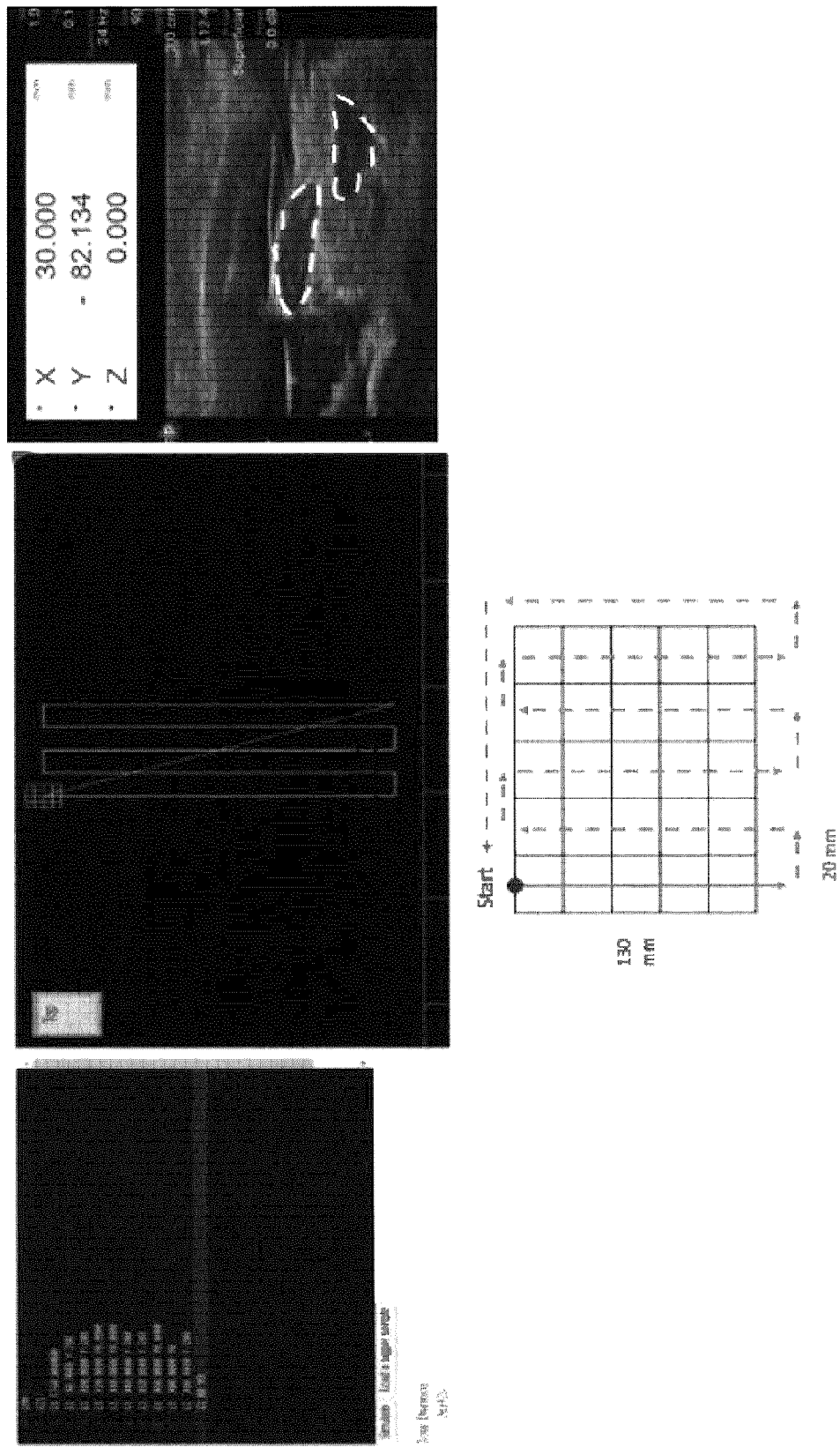
FIG. 15 shows a correlation of the ultrasound scans with a cartesian coordinate system. The videos of the ultrasound scans of the specimen are captured and then sent to the radiologist for lymph node identification. The radiologist would take note of the suspected lymph nodes in the videos and then provide us with images, where the lymph nodes are correlated to coordinates in XY space where the frame of the scan was captured.

Analysis of Ultrasound Videos:

The recorded ultrasound videos were sent to a radiologist, who was unaware (blinded) of the location of the LNs. The radiologist was instructed to identify LNs based on their shape and echogenicity (compared with that of the surrounding fatty tissues), and then screenshot and mark the LNs for downstream data analyses (FIGS. 14 and 15). In alternative examples of LN identification in ultrasound scan data, image data captured from the ultrasound scan is inspected by either one or both of machine learning or rule-based image processing (i.e., edge detection) algorithms that will help detect LNs and other relevant biological structures in the resected specimen-ultimately eliminating the requirement of a radiologist in this particular step for our device.

Marking System:

Although the tissue pen or the pin gun was not used in the current experiment, alternative examples for this device can optionally include a marking tool that can physically and/or visually mark suspected LN locations in distinct regions of the tissue specimen (following processing of the recorded ultrasound videos via radiologist image selection or rules-based or machine learning algorithms of image classification). If the tissue pen is used for this process, then a refillable pen can be used with available tissue-marking dyes in the pathology laboratory (i.e., Royal India Ink). While, if an automated pin gun is used, then pathology dissection pins could be incorporated into a pneumatic, hydraulic or motor-powered pin gun. For both mechanisms, the end-effector mounted at the end of the robotic arm could be programmed for motorized control to mark identified target regions on the tissue specimen.

Figure 16:
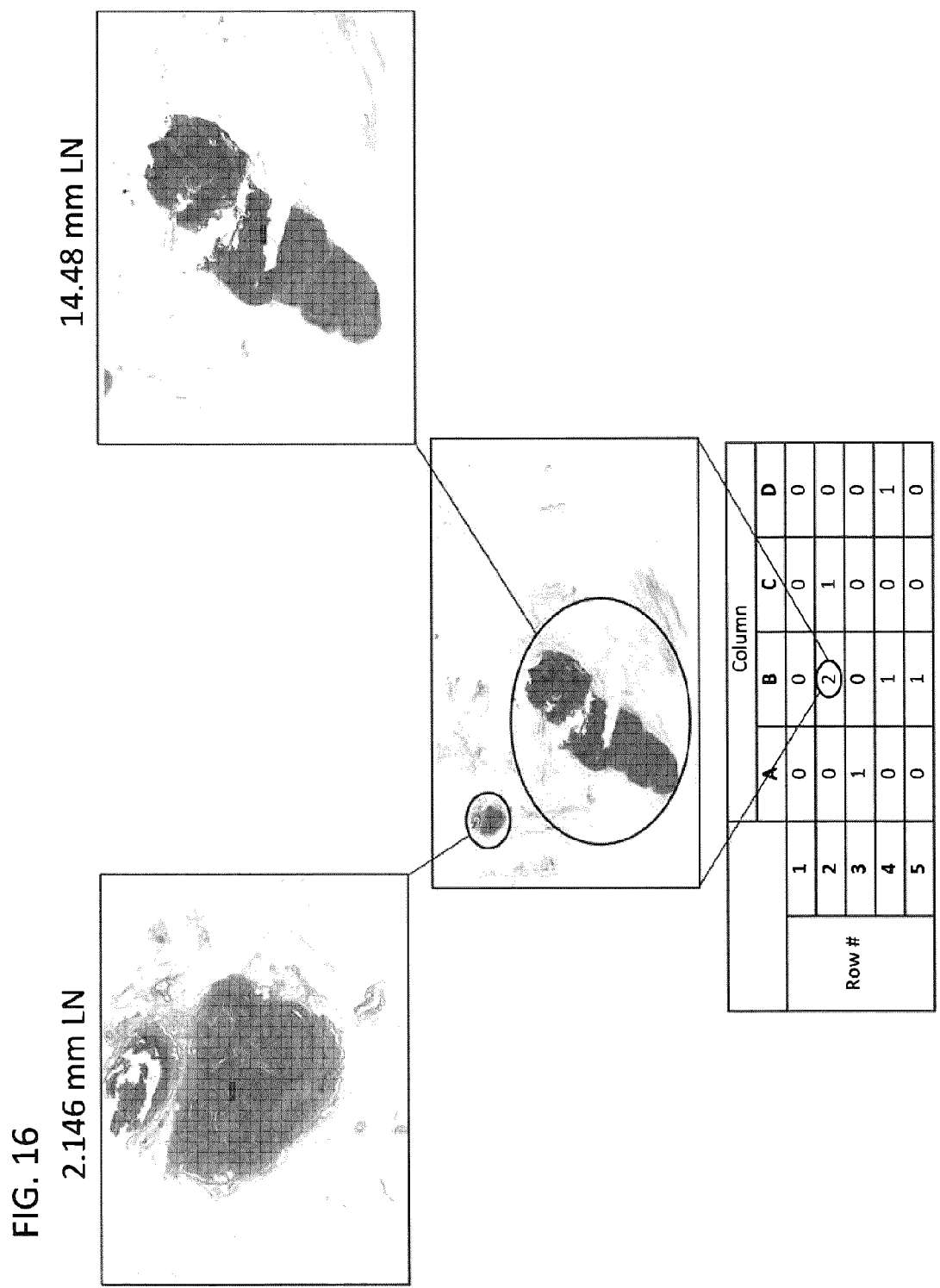
FIG. 16 shows histology findings from a representative sample. H&E staining of the 2 LNs in B2 reveal specific histological structures that can be observed using a light microscope. The transverse diameters of the 2 LNs were ~2 mm and ~14 mm.

Hematoxylin and Eosin (H&E) Staining:

All tissues from the specimen were submitted for further histological processing, and their relative locations in the 2 by 2 cm grid were noted. Tissues were excised, fixed in 10% buffered formalin solution and embedded, and sectioned into 5 μm-thick sections. The tissue sections were then stained with H&E for routine histology. A blinded pathologist evaluated whether histological structures of LNs were present using a light microscope and the images were captured (Nikon, Japan). The transverse diameters of the LNs and their relative locations on the grid were also noted (FIG. 16).

Downstream Data Analyses:

We cross-correlated the independent and blinded findings from the radiologist and pathologist and then conducted additional analyses that examined sensitivity (the ability of a test to correctly identify a square/block with LNs), specificity (the ability of the test to correctly identify a block without LNs), accuracy (overall agreement between the gold standard [H&E staining] and the test), positive predictive value (the likelihood that the block sent to histology is positive for LNs), and negative predictive value (the likelihood that the block sent to histology is negative for LNs) (FIG. 17). The statistical differences between the sensitivity and specificity of the device and histology findings were also calculated (two-sided P-value of <0.0001 by Fisher's exact test).

Results

Ultrasound Scans and Histopathologic Findings

Based on the ultrasound videos, the radiologist was able to identify 7 suspected LNs that presented with distinct hypoechoic features relative to the surrounding fatty tissues (appeared hyperechoic). In reference to the 2 by 2 cm grid system, the radiologist identified 1 LN in A3 (column A, row 3), 2 LNs in B2, 1 LN in B4, 1 LN in B5, 1 LN in C2, and another LN in D4. Interestingly, the location of the 7 suspected LNs were also confirmed via histologic examination. Microscopic analyses additionally determined the presence of various sized LNs in the specimen. For example, the transverse diameters of the 2 LNs in B2 were 2.146 mm and 14.48 mm (FIG. 16)—further corroborating the capabilities of an ultrasound solution in detecting LNs less than 5 mm.

Performance parameters were also calculated based on the radiologist's ability to detect potential LNs in each 2 by 2 cm square using the ultrasound videos. The radiologist was able to identify 6 'positive' blocks with potential LNs out of 14 'negative' blocks that potentially do not contain LNs, which were identical to the findings from histology (FIG. 18). Based on a sample size of 20 blocks, the sensitivity, specificity, accuracy, positive and negative predictive values equaled to 100%. As well, statistical differences between the sensitivity and specificity of the device's ultrasound findings and histology are significant (two-sided P-value of <0.0001 by Fisher's exact test; sensitivity value=1.0, 95% CI=0.6097 to 1.0; and specificity value=1.0, 95% CI=0.7847 to 1.0).

Advantages of ultrasonography to detect LNs.

Although the application of ultrasound imaging has not yet been used for the identification of LNs in resected specimens (and the pathology field in general), the role of ultrasound in the assessment of cervical lymphadenopathy is well-established, where ultrasound features are used by the radiologist to help identify abnormal LNs in the necks of patients with head and neck carcinomas [1-3]. In particular, high-resolution, real-time sonography allows the radiologist to examine the shape, size, echogenic hilius, sharp nodal borders, hypoechogenicity, coagulation necrosis and even intranodal calcifications of LNs [2]. Interestingly, one study has also shown that (manual) ultrasound examination is highly sensitive (96.8%) in identifying cancer positive LNs in the neck compared to manual palpation (73.3%), while the combination of ultrasound examination with fine-needle aspiration biopsy allowed for a more accurate assessment of nodal disease in head and neck cancers (a sensitivity of 95.7% and a specificity of 92.9%) [1]. Furthermore, other imaging modalities (computed tomography and magnetic resonance imaging) can also be used for the evaluation of cervical LNs, but these tools can be less sensitive than ultrasound in detecting LNs less than 5 mm in diameter, while ultrasound is capable of detecting LNs less than 2 mm in diameter [2,4].

Figure 19:
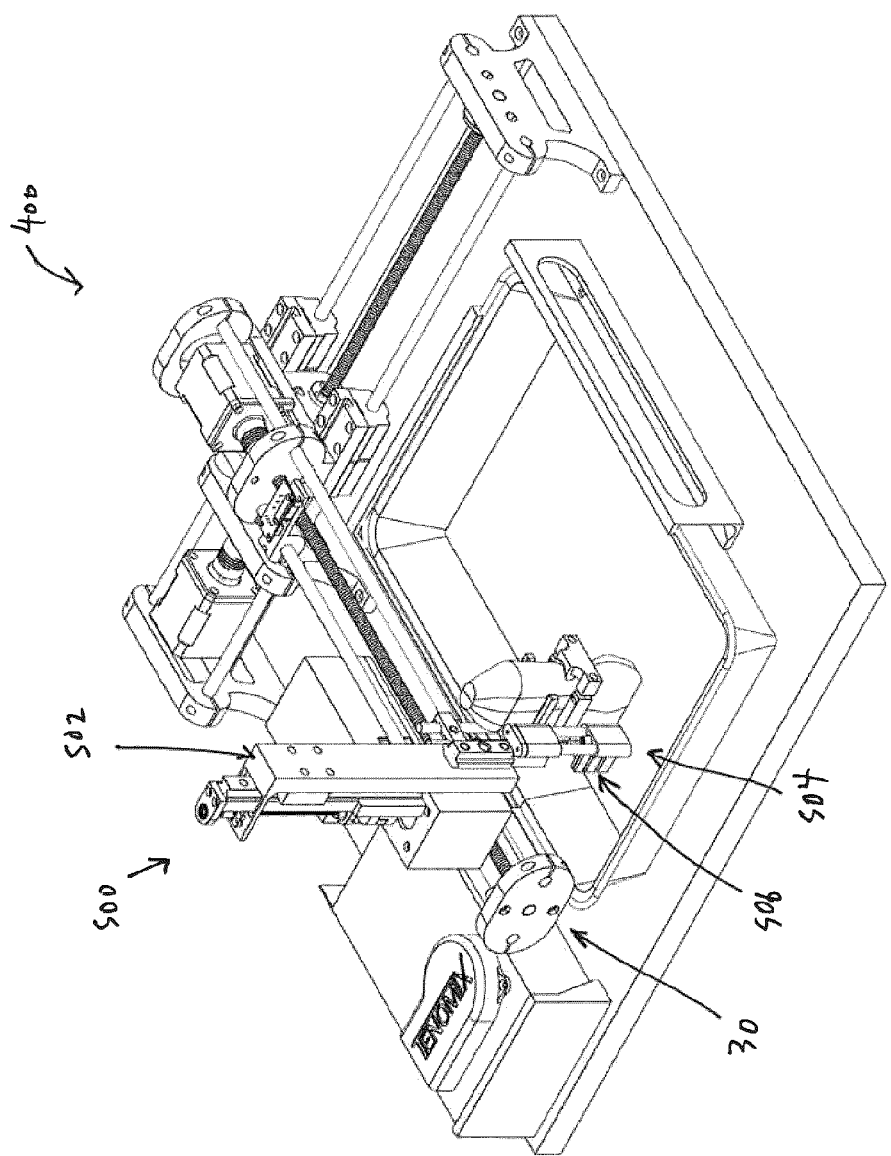
FIG. 19 is a view similar to FIG. 2 showing another embodiment of the invention
Figure 20:
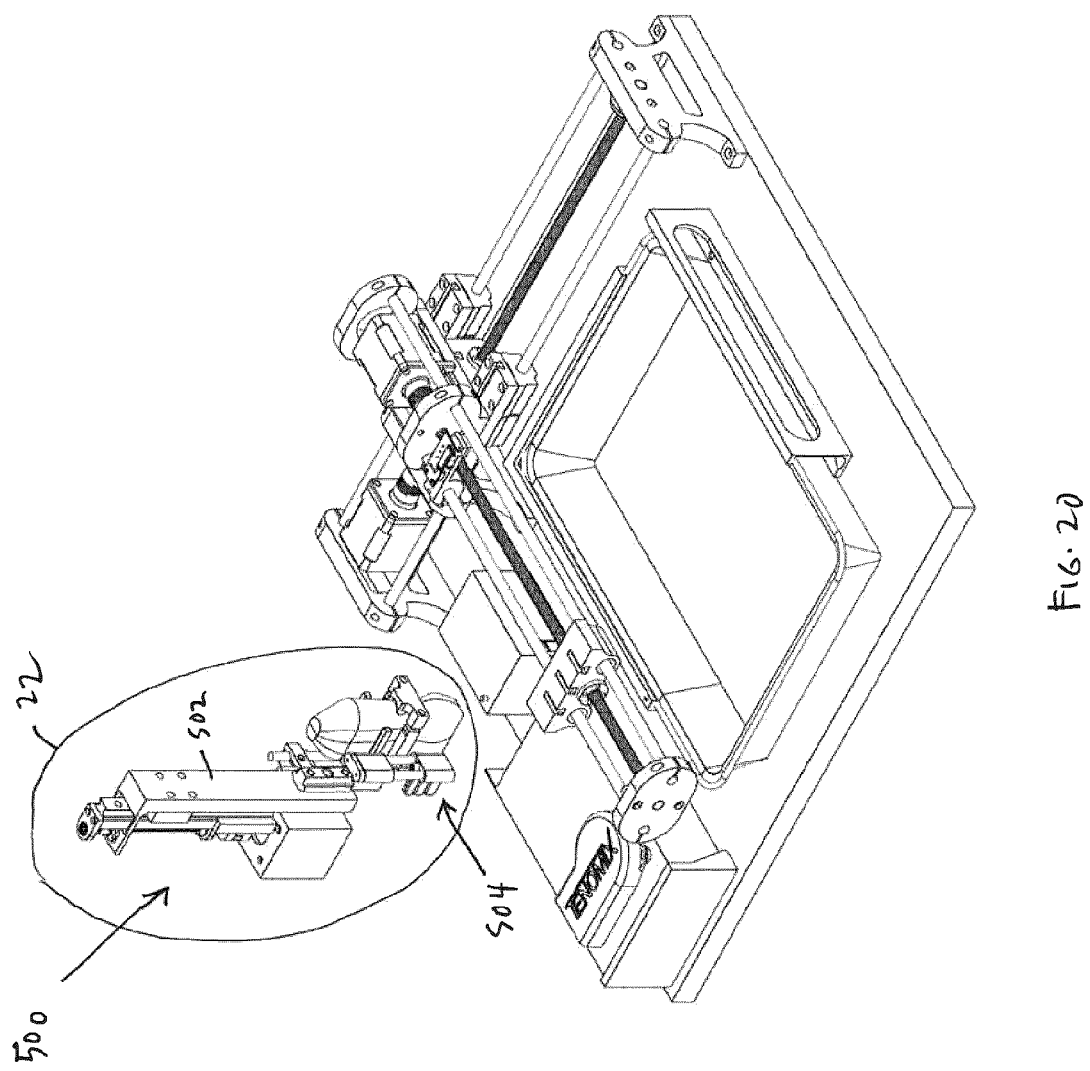
FIG. 20 is an exploded view of FIG. 19
Figure 21:
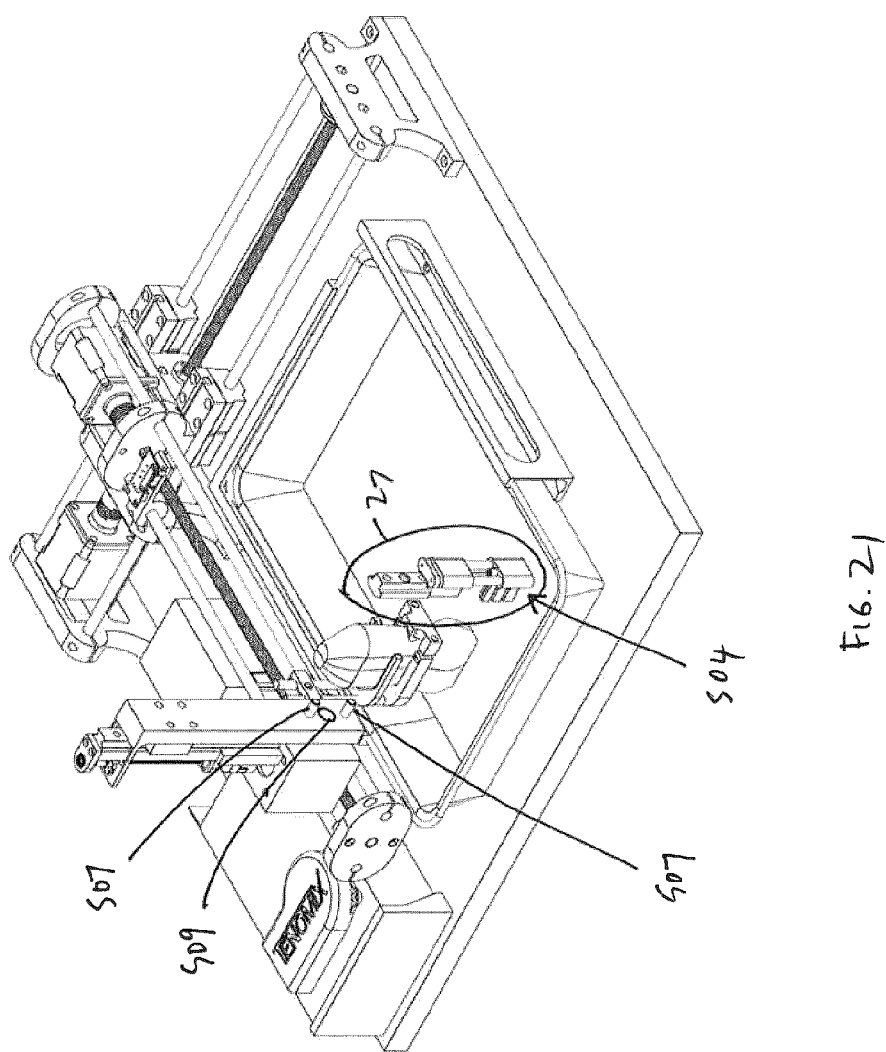
FIG. 21 is another exploded view of FIG. 19.
Figure 22:
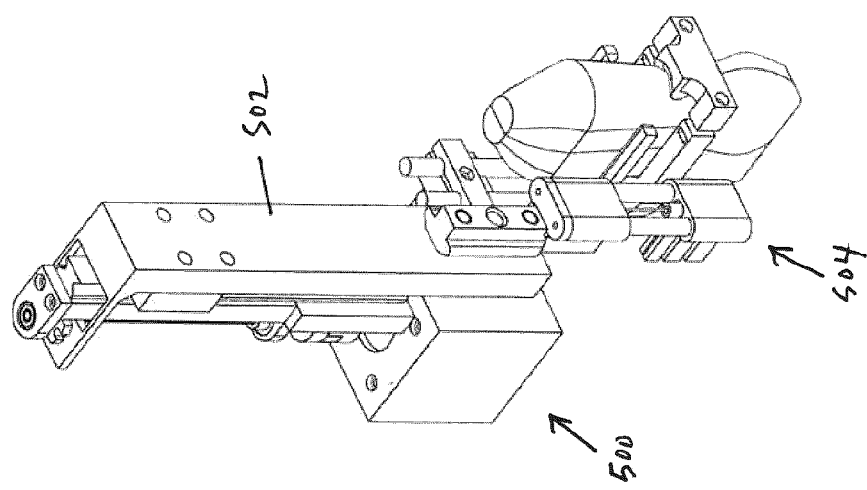
FIG. 22 is an enlarged view of encircled area 22 of FIG. 20.
Figure 34:
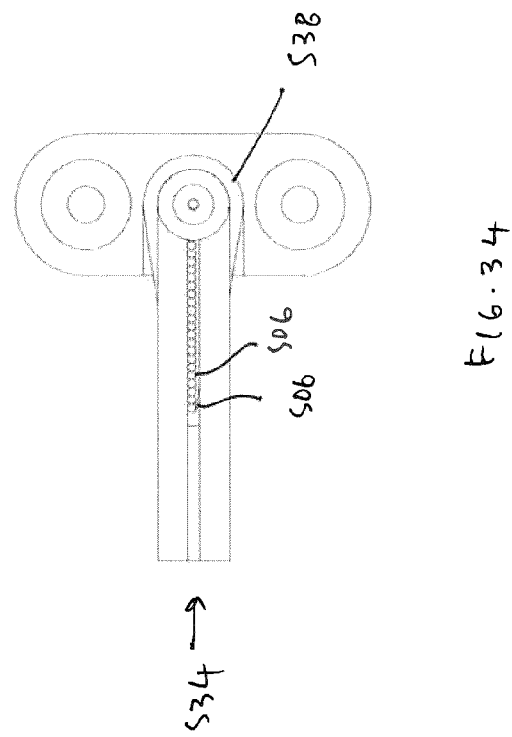
FIG. 34 is a view along section 34-34 of FIG. 28.
Figure 33:
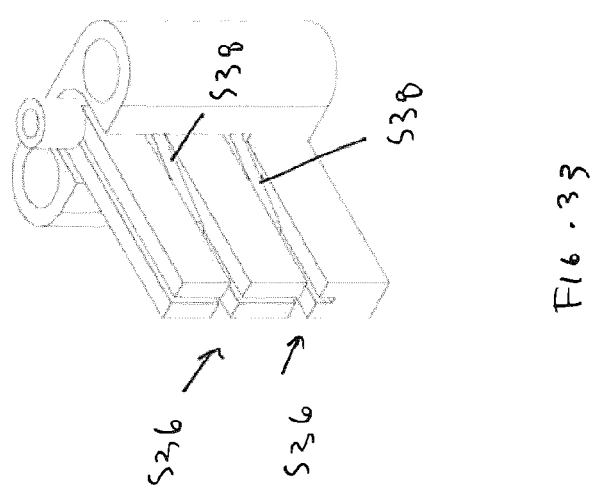
FIG. 33 is a view of the structure of encircled area 33 in FIG. 27.

FIGS. 19 through 21 show another embodiment of the invention. This embodiment includes:

all of the structure of FIG. 1, indicated generally as 400 a linear actuator 500;

an L-shaped block 502;

a tissue marking device 504; and a plurality of pins 506.

In this embodiment: the linear actuator 500 is formed integrally with gripper arm 36 (not shown) and moves therewith on the moveable arm 30; the probe is an Interson linear array transducer (Pleasanton, CA, US)A, 10-20 MHZ; and the transporter is configured to convey the probe at 100 mm/min.

The L-shaped block 502 is mounted to the linear actuator 500 for selective vertical movement relative to the moveable arm 30, has protruding therefrom a pair of dowels 507 and has a magnet 509

The tissue marking device 504 will be seen in FIGS. 27 to 30 to have a mount 508, a shuttle 510 and a pair of elastics 512.

The mount 508 includes a magnet 514, a striker pin 516, and a pair of hooks 518, and defines a pair of sockets 520 and a pair of cylinders 522.

The shuttle 510 includes a pair of pistons 524, a top cap 526 and a magazine 528.

The pistons 524 are received by the cylinders 522.

The top cap 526 couples the pistons 524 to one another and has a pair of hooks 530 protruding therefrom.

The magazine 528 couples the pistons 524 to one another, defines a barrel 532 which is coincident with the axis of the striker pin 516, has a chamber 534 which communicates with the barrel 532, has a pair of slots 536 and has, in each slot, an elastic 538.

The plurality of pins 506 are disposed in the chamber and are urged towards the barrel 532 by elastics 538.

The pair of elastics 512 are engaged by the hooks 518 on the mount 508 and the hooks 530 on the top cap 526, to bias the top cap 526 for movement towards the cylinders 522.

In use, the sockets 520 in the mount 508 receive the dowels 507 of the L-shaped block 502 and the magnet 514 in the mount 508 urges the mount 508 towards the magnet 509 in the L-shaped block 502, thereby to mount the tissue marking device 504 to the L-shaped block 502, as indicated by the sequence of FIGS. 21, 19.

The manner in which the tissue marking device 504 operates will be evident upon a review of the sequence of FIGS. 23 through 26.

FIG. 23 shows the L-shaped block 502 fully raised. It will be appreciated that in this configuration, the tissue marking device 504 can be conveyed to any desired location over the tissue sample by the gantry.

FIG. 24 shows the L-shaped block 502 lowered from its position in FIG. 23. It will be appreciated that, as the block 502 is lowered, the magazine 528 will eventually encounter the tissue sample, which will restrict further downward movement of the magazine 528.

FIG. 25 shows the L-shaped block 502 lowered further from its position in FIG. 24, but with magazine fixed in position (as would occur when tissue was encountered). Here, it will be understood that the striker pin 516 has entered the barrel 532 (neither shown) and urged one of the pins 506 out of the barrel 532 (and into the tissue).

FIG. 26 shows the L-shaped block 502 raised from its position in FIG. 25; so raised, providing clearance from the tissue, elastics 512 have urged the magazine 528 downwardly.

An advantageous use of the aforedescribed structure is as part of a method which forms another aspect of the invention and includes four distinct workflows, as described below Scanning In this workflow, the following steps are completed, typically by a laboratory technician: receive or prepare a tissue sample; immobilize the tissue sample in a tray by placing dissection pins through the tissue into the corkboard; place the tray in the apparatus of FIG. 19; enter detail of the tissue sample and the tray into a database; and initiate a scan wherein the apparatus automatically conveys the probe over the tissue sample to capture a complete ultrasound image of the tissue sample. When the scan is complete: the ultrasound image is placed in an identifying queue maintained by the database and associated with the details of the tray and the tissue sample.

Identifying

In this workflow, the following steps are carried out, by, for example, a radiologist, at a location remote from the laboratory, using a computing facility: review an ultrasound image from the queue and identify areas of interest in the selected image that have a radiological resemblance to a lymph node. When the review is complete, a set of locations associated with the scan and thereby associated with the sample and the tray, is placed in a marking queue; the scan and tray/sample identifiers are moved from the identifying queue to the marking queue.

Marking

In this workflow, the following steps are completed, typically by a laboratory technician: initiate a marking operation in respect of a tray/sample in the marking queue. In this workflow, locations associated with the sample are automatically marked. Upon completion of the marking step, the tray/sample and associated scan are removed from the marking queue and placed in an extraction queue.

Extraction

In this workflow, a lymph node analysis of a marked tissue is performed, typically by a laboratory technician; by virtue of the markings, the technician may focus efforts. As part of this step, the tray/sample and associated scan are removed from the extraction queue.

Variations

Figure 35:
FIG. 35 is a view of a radiology interface of a computing facility which forms part of another embodiment of the invention.
Figure 36:
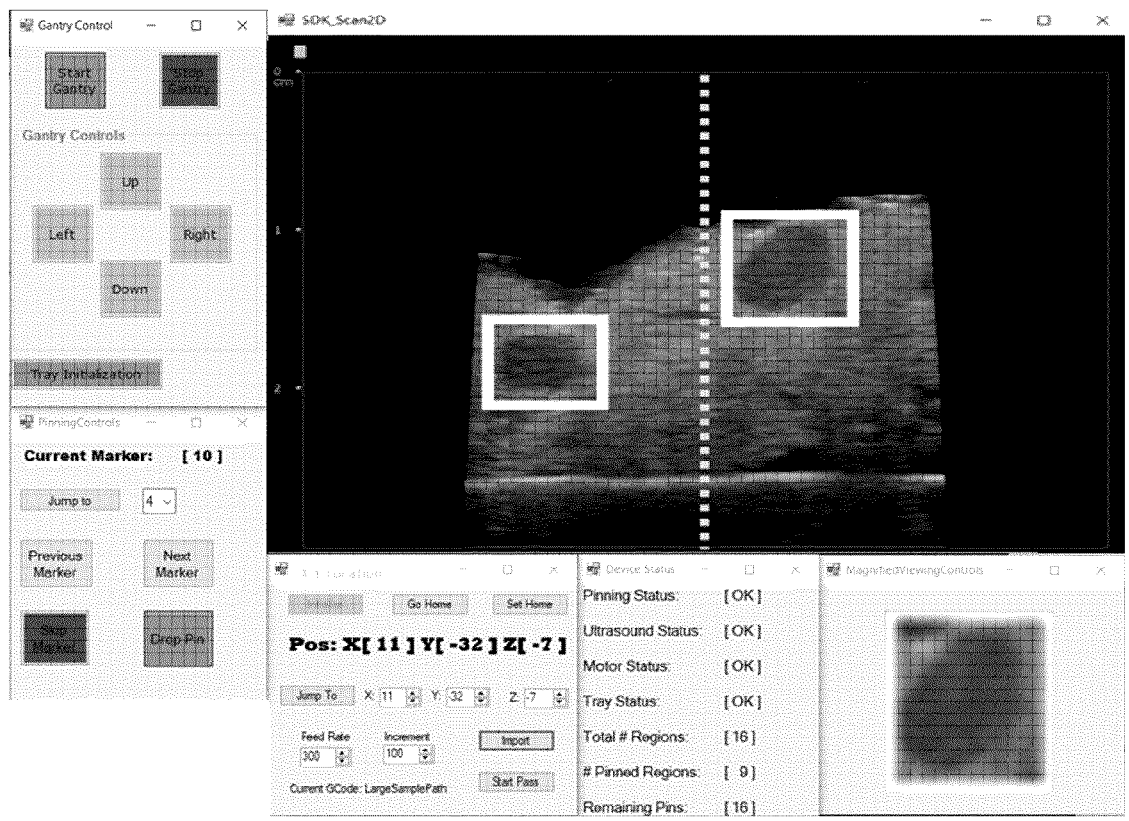
FIG. 36 is a view of a data entry interface of the computing facility.

Variations to the above workflow are possible, without limitation: other probes and marking devices could be used; the marking operation need not be done automatically; and the apparatus for the marking and the scanning need not be one and the same Graphic User Interfaces FIG. 35 shows a user interface in a computing functionality that is used in the Scanning Step in the above method. The laboratory technician inputs details of the sample [i.e. patient and tray] using the depicted data entry screen and selects "confirm". This triggers the presentation of the interface shown in FIG. 36. On this interface the technician selects "Tray initialization" button, which causes the device to conduct internal checks to ensure a tray is in place, check the status of the probe and motors for operability, scan the dimensions of the sample as well as its position relative to the tray/gantry and calculate a sweeping path that brings the probe into scanning proximity of the entirety of the specimen [having regard to the scanning capability of the probe with respect to the specimen]. Once the device has calculated the path and confirmed machine status, the machine will signal "OK". From there, the technician will select "Start Gantry", where the device will cause the probe to traverse the sweeping path and capture a complete ultrasound image of the sample which will be stored in a database and associated with the entered details to permit the technician to identify the tray and sample at a later date. When the scan is complete, the gantry system will automatically navigate back to its global home coordinates/position, the motors and probe will be disabled, to permit safe removal and suitable (cold) storage of the sample and the stored tray/sample details and scan will be placed in the identifying queue.

Figure 37:
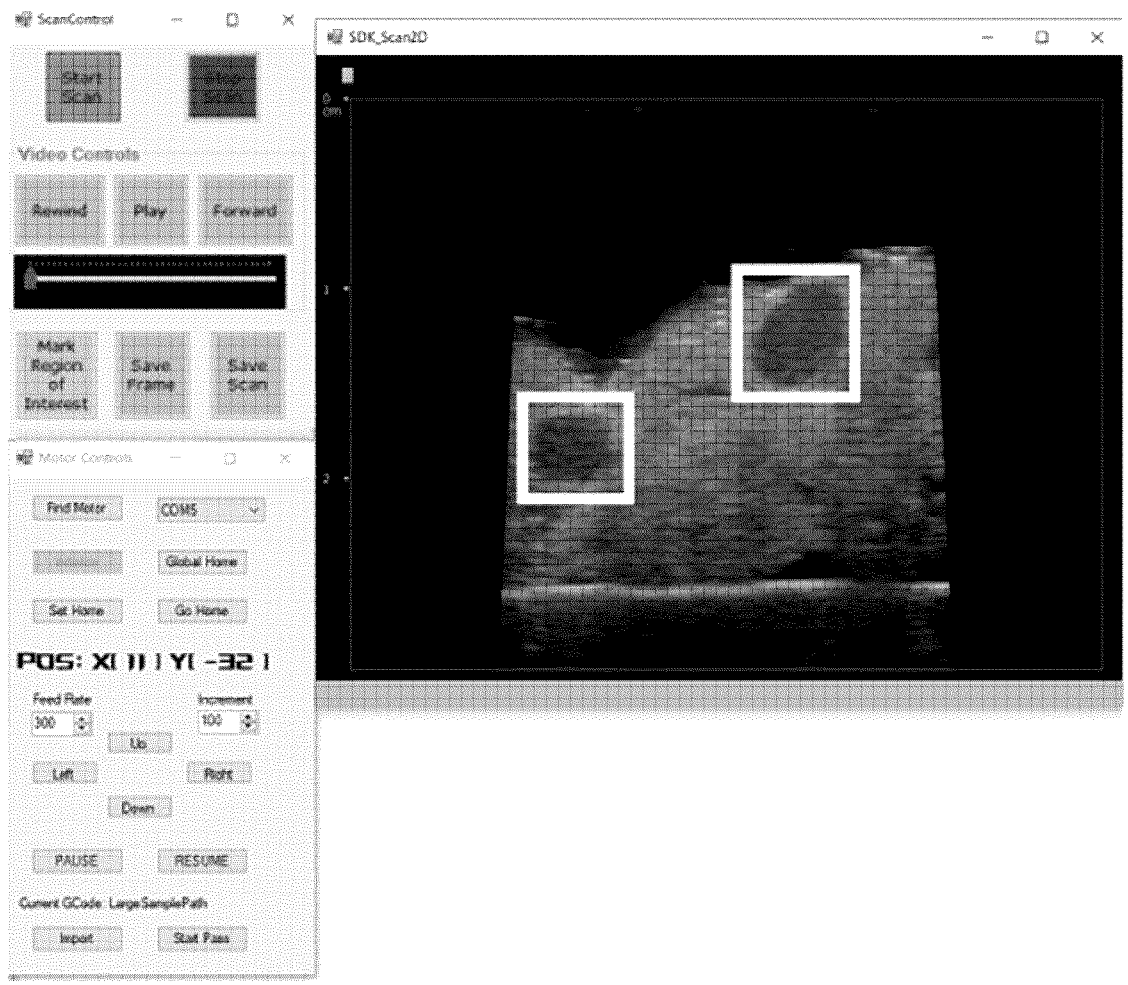
FIG. 37 is a view of a technician interface of the computing facility.

FIG. 37 depicts a user interface in the computing functionality that is used in the Identifying step in the above method. The interface will be seen to include a series of buttons ['play, 'forward', 'stop' and 'rewind'] that are used by the radiologist to review a the previously stored ultrasound image [following the path of the probe in the automated scan of the tissue]. When a structure that radiologically resembles a lymph node is seen, the 'Mark Region of Interest' button can be selected, which will allow the radiologist to use a cursor to drag and drop a frame over the suspected lymph node (demonstrated by the white boxes). The creation of a frame creates a location, calculated as the center of the frame. When the Identifying effort is completed, the reviewer selects "Save Scan", which places the list of locations created in the marking queue.

The interface in FIG. 35 is also used in the Marking step in the above method. More particularly, it will be appreciated that this interface is presented after the technician has entered identifiers that match those previously stored in association with a completed scan. Selecting the 'Tray Initialization' button again causes the device to perform a diagnostic to ensure that the device is active and a tray is correctly placed. The device will again scan the sample and extract size and shape. However, in this step, the computing functionality will confirm that the size and shape match that previously on file in association with the tray/sample. Once these internal checks have been completed, the technician can navigate the marking device to each of the stored locations using the "Jump to", "Previous Marker", or "Next Marker" buttons. The Region of Interest associated with the selected location will be automatically displayed in the Magnified Viewing Controls. Selection of the "Drop Pin" button causes the device to place a pin and advance to the next stored location; selection of the "Skip Marker" button causes the device to advance to the next location without placement of a pin. Selection of the 'Stop Gantry' button causes the device to remove the scan from the marking queue and into the extraction queue, move the gantry to its global home coordinates/position and disengage the motors to permit removal of the tray Competitive Advantages and Differentiation.

The technology may offer one or more significant competitive advantages over existing LN dissection methods, including:

Significant time savings in grossing per sample, less labour intensive

Better ergonomics for pathology staff

A simple and safe design that allows for easy cleaning and maintenance

Accurate identification of LNs in a sample

Non-destructive testing method, which will retain the original bulk structure of the resected tissue specimen and allow pathology staff to revisit the specimen at a later date if needed as required by standard protocols Reductions in pathology 'waste' and resources (i.e., less 'false negative' tissue cassettes being submitted for processing)

Documentation of the original location of LNs in a specimen prior to dissection

Improvements in diagnostic turnaround times, laboratory efficiency and specimen throughput without the need for re-grossing/re-pulling Better differentiation of LNs, tumour deposits and vascular invasions Increase LN yields Improvements in the collection of surgical and pathology quality indicator metrics Adequate LN sampling is met, which can contribute to accurate cancer staging for patients, timely and correct cancer treatment Provides more control of the LN dissection process to the dissector, where marked LN locations made by the device can be double checked by the dissector prior to submitting the tissue area for further processing Potential applications to other resected cancer tissues requiring careful LN dissections.

Several illustrative variants of a lymph node locating device, method or system have been described above. Further variants and modifications are described below. Moreover, guiding relationships for configuring variants and modifications are also described below. Still further variants and modifications are contemplated and will be recognized by the person of skill in the art. It is to be understood that guiding relationships and illustrative variants or modifications are provided for the purpose of enhancing the understanding of the person of skill in the art and are not intended as limiting statements.

For example, while a Cartesian robot gantry is exemplified and Cartesian coordinates are straightforward for most contemplated implementations, the device, system and method can accommodate non-linear coordinate systems, such as polar or cylindrical coordinates. For example, if the scanning of the resected tissue sample and subsequent image analysis benefits from circular interpolation, polar coordinates might be more convenient than Cartesian coordinates. Although Cartesian coordinates can be used in three dimensions (x, y, and z), polar coordinates only specify two dimensions (r and θ). If a third axis, z (height), is added to polar coordinates, the coordinate system is referred to as cylindrical coordinates (r, θ, z).

As another example, the Cartesian coordinates may be implemented in two dimensions or three dimensions as desired for a specific implementation. For example, a two dimension Cartesian coordinate implementation suffices when all scan path positions of the ultrasound probe are constrained to a single plane. However, a three dimension Cartesian coordinate implementation may be used when scan path positions of the ultrasound probe are desired in a plurality of distinct planes.

As another example, the moveable gantry may accommodate any linear actuator and need not be limited to a lead screw and lead nut versions of linear actuators.

As another example, the movable gantry may take any form including for example, articulated arms and control of motion of the moveable gantry may be achieved with any suitable computer control.

Whereas corkboard is indicated to be used as a liner for the tray, other materials that minimize or avoid acoustic reflections off the bottom of the tray can be used in the context of ultrasound probes.

As another example, the computer control of the moveable gantry can be configured with a manual override option to manually modify the computer controlled actuation of the moveable gantry. As a further example, a minimal implementation of the moveable gantry may be devoid of computer control and may be actuated by manual manipulation (for example, manipulation of actuating knobs or dials) with position coordinates indicated by calibrated markings or by digital position data provided by position encoders or sensors coupled to the moveable components of the moveable gantry.

As another example, a composite representation of the entire volume of the tissue specimen may be generated from the ultrasound scan data. The composite representation may show a 3D volume or a 2D area as desired for a specific implementation. The composite representation may benefit medical assessment of a selected lymph node region of interest and surrounding anatomical features such as vascular features. A computer generated grid may be registered to the composite representation. The composite representation may benefit co-registration of the entire tissue sample.

Embodiments disclosed herein, or portions thereof, can be implemented by programming one or more computer systems or devices with computer-executable instructions embodied in a non-transitory computer-readable medium. When executed by a processor, these instructions operate to cause these computer systems and devices to perform one or more functions particular to embodiments disclosed herein. Programming techniques, computer languages, devices, and computer-readable media necessary to accomplish this are known in the art.

In an example, a non-transitory computer readable medium embodying a computer program for lymph node locating may comprise: computer program code for obtaining ultrasound scan data of a resected tissue sample comprising a plurality of image frames captured during acquisition of the ultrasound scan data and a plurality of position coordinates recorded during acquisition of the ultrasound scan data; computer program code for registering each of the plurality of image frames to a unique one of the plurality of position coordinates so that each of the plurality of image frames is registered to a unique position coordinate; and computer program code for selecting at least one image frame showing a lymph node and recording the selected image frame as a lymph node region of interest with its associated unique position coordinate.

In another related example, the computer readable medium further comprises computer program code for acquiring the ultrasound scan data by automated computer controlled actuation of a moveable gantry holding an ultrasound probe to move the ultrasound probe along a scan path to image the resected tissue sample. In yet another related example, the computer readable medium further comprises computer program code for marking the selected lymph node region of interest in the resected tissue sample by automated computer controlled actuation of a moveable gantry holding a marking tool to move the marking tool to the unique position coordinate relative to the resected tissue sample. In still another related example, the computer readable medium further comprises computer program code for excising the selected lymph node region of interest from the resected tissue sample by automated computer controlled actuation of a moveable gantry holding a dissection tool to move the dissection tool to the unique position coordinate relative to the resected tissue sample.

The computer readable medium is a data storage device that can store data and computer executable instructions, which can thereafter, be read by a computer system. Examples of a computer readable medium include read-only memory, random-access memory, CD-ROMs, magnetic tape, optical data storage devices and the like. The computer readable medium may be geographically localized or may be distributed over a network coupled computer system so that the computer readable code is stored and executed in a distributed fashion.

Computer-implementation of the system or method typically comprises a memory, an interface and a processor. The types and arrangements of memory, interface and processor may be varied according to implementations. For example, the interface may include a software interface that communicates with an end-user computing device through an Internet connection. The interface may also include a physical electronic device configured to receive requests or queries from a device sending digital and/or analog information. In other examples, the interface can include a physical electronic device configured to receive signals and/or data relating to the lymph node locating device, method or system, for example from an imaging scanner or image processing device or a gantry controller.

Any suitable processor type may be used depending on a specific implementation, including for example, a microprocessor, a programmable logic controller or a field programmable logic array. Moreover, any conventional computer architecture may be used for computer-implementation of the system or method including for example a memory, a mass storage device, a processor (CPU), a Read-Only Memory (ROM), and a Random-Access Memory (RAM) generally connected to a system bus of data-processing apparatus. Memory can be implemented as a ROM, RAM, a combination thereof, or simply a general memory unit. Software modules in the form of routines and/or subroutines for carrying out features of the system or method can be stored within memory and then retrieved and processed via processor to perform a particular task or function. Similarly, one or more method steps may be encoded as a program component, stored as executable instructions within memory and then retrieved and processed via a processor. A user input device, such as a keyboard, mouse, or another pointing device, can be connected to PCI (Peripheral Component Interconnect) bus. If desired, the software may provide an environment that represents programs, files, options, and so forth by means of graphically displayed icons, menus, and dialog boxes on a computer monitor screen.

For example, any number of blood flow images and blood flow characteristics may be displayed, including for example a time-enhancement curve.

Computer-implementation of the system or method may accommodate any type of end-user computing device including computing devices communicating over a networked connection. The computing device may display graphical interface elements for performing the various functions of the system or method, including for example display of a selected image frame showing a lymph node region of interest. For example, the computing device may be a server, desktop, laptop, notebook, tablet, personal digital assistant (PDA), PDA phone or smartphone, and the like. The computing device may be implemented using any appropriate combination of hardware and/or software configured for wired and/or wireless communication. Communication can occur over a network, for example, where remote control of the system is desired.

If a networked connection is desired the system or method may accommodate any type of network. The network may be a single network or a combination of multiple networks. For example, the network may include the internet and/or one or more intranets, landline networks, wireless networks, and/or other appropriate types of communication networks. In another example, the network may comprise a wireless telecommunications network (e.g., cellular phone network) adapted to communicate with other communication networks, such as the Internet. For example, the network may comprise a computer network that makes use of a TCP/IP protocol (including protocols based on TCP/IP protocol, such as HTTP, HTTPS or FTP).

Embodiments described herein are intended for illustrative purposes without any intended loss of generality. Still further variants, modifications and combinations thereof are contemplated and will be recognized by the person of skill in the art. Accordingly, the foregoing detailed description is not intended to limit scope, applicability, or configuration of claimed subject matter.

REFERENCE LIST

1. Jong, R. J. B., Rongen, R. J., Lameris, J. S., Harthoorn, M., Verwoerd, C. D. A., & Knegt, P. (1989). Metastatic Neck Disease: Palpation vs Ultrasound Examination. Archives of Otolaryngology—Head and Neck Surgery, 115(6), 689-690. http://doi.org/10.1001/archotol.1989.01860300043013
2. Ahuja, A., & Ying, M. (2000). Grey-scale sonography in assessment of cervical lymphadenopathy: Review of sonographic appearances and features that may help a beginner. British Journal of Oral and Maxillofacial Surgery, 38(5), 451-459. http://doi.org/10.1054/bjom.2000.0446
3. Ahuja, A. T., Ying, M., Ho, S. Y., Antonio, G., Lee, Y. P., King, A. D., & Wong, K. T. (2008). Ultrasound of malignant cervical lymph nodes. Cancer Imaging. http://doi.org/10.1102/1470-7330.2008.0006
4. Som, P. M. (1992). Detection of metastasis in cervical lymph nodes: CT and MR criteria and differential diagnosis. American Journal of Roentgenology. http://doi.org/10.2214/ajr.158.5.1566697
5. Casarotto, R. A., Adamowski, J. C., Fallopa, F., & Bacanelli, F. (2004). Coupling Agents in Therapeutic Ultrasound: Acoustic and Thermal Behavior. Archives of Physical Medicine and Rehabilitation, 85(1), 162-165. http://doi.org/10.1016/S0003-9993(03)00293-4
6. Gibson, J. A., & Odze, R. D. (2019). Tissue Sampling, Specimen Handling, and Laboratory Processing. In Clinical Gastrointestinal Endoscopy (pp. 51-68.e6). http://doi.org/10.1016/b978-0-323-41509-5.00005-0
7. Knoblaugh, S. E., & Randolph-Habecker, J. (2018). Necropsy and Histology. In Comparative Anatomy and Histology (pp. 23-51). http://doi.org/10.1016/b978-0-12-802900-8.00003-8
8. Richards, P. S., & Peacock, T. E. (2007). The role of ultrasound in the detection of cervical lymph node metastases in clinically N0 squamous cell carcinoma of the head and neck. Cancer Imaging, 7(1), 167-178. http://doi.org/10.1102/1470-7330.2007.0024
9. Carovac, A., Smajlovic, F., & Junuzovic, D. (2011). Application of Ultrasound in Medicine. Acta Informatica Medica, 19(3), 168. http://doi.org/10.5455/aim.2011.19.168-171
10. Bertocci, F., Grandoni, A., & Djuric-Rissner, T. (2019). Scanning acoustic microscopy (SAM): A robust method for defect detection during the manufacturing process of ultrasound probes for medical imaging. Sensors (Switzerland), 19(22). http://doi.org/10.3390/s19224868
11. D. Dance, S. Christofides, M. Maidment, I. M. (2014). Diagnostic Radiology Physics: A handbook for teachers and students, Iaea, 710. Retrieved from http://www-pub.iaea.org/books/IAEABooks/8841/Diagnostic-Radiology-Physics-A-Handbook-for-Teachers-and-Students?utm_content=buffer89b0e&utm_medium=social&utm_source=twitter.com&utm_campaign=buffer
12. Yu, H. (2020). Scanning acoustic microscopy for material evaluation. Applied Microscopy, 50(1), http://doi.org/10.1186/s42649-020-00045-4.

The invention claimed is:

1. A system for use with a tissue sample, the system comprising a tray for receiving the tissue sample in use and an apparatus, the apparatus including:
a support which receives the tray in use;
a probe adapted to transmit waves and identify wave echoes;
a tissue marking device; and
a transporter adapted to:
convey the probe over the tissue sample in use, the probe and the transporter being adapted such that, in use, information about the tissue sample is collected sufficient to permit a radiologist to identify structures which resemble lymph nodes in the tissue sample; and
convey the tissue marking device to locations of interest which correspond to the locations of structures which resemble lymph nodes in the tissue sample.

2. The system of claim 1, wherein the probe is an ultrasound probe and the transporter is adapted to automatically convey the probe to capture a complete ultrasound image of the tissue sample.

3. The system of claim 1, further comprising a computing facility adapted to:
permit the complete ultrasound image to be viewed on a screen; and
permit a viewer to make, on the screen and with one or more of a mouse, stylus, keyboard or touchscreen interface, selections, each selection being a structure which resembles a lymph node; and
generate the locations of interest based upon the selections.

4. The system of claim 1, wherein the transporter is adapted to automatically convey the tissue marking device to each of the locations of interest and the tissue marking device is adapted to automatically place a mark at each of the locations of interest.

5. The system of claim 1, wherein the transporter system comprises an X-Y table.

6. The system of claim 1, wherein the tissue marking device is a pin setter.

7. The system of claim 1, further comprising a computing facility and wherein:
the probe is an ultrasound probe and the transporter is adapted to automatically convey the probe to capture a complete ultrasound image of the tissue sample;
the computing facility is adapted to:
permit the complete ultrasound image to be viewed on a screen; and
permit a viewer to make, on the screen and with one or more of a mouse, stylus, keyboard or touchscreen interface, selections, each selection being a structure which resembles a lymph node; and
generate the locations of interest based upon the selections;
the transporter is adapted to automatically convey the tissue marking device to each of the locations of interest and the tissue marking device is adapted to automatically place a mark at each of the locations of interest.

8. A method for use with a tissue sample, the method comprising:
immobilizing the sample in a tray;
automatically conveying a probe adapted to transmit waves and identify wave echoes over the tissue sample to collect information about the tissue sample sufficient to permit a radiologist to identify structures which resemble lymph nodes in the tissue sample;
identifying locations of interest in the sample using the information, each location of interest corresponding to the location of a structure which has a radiologic resemblance to a lymph node; and
automatically marking each of the locations of interest by automatically conveying a marking device thereto.

9. The method according to claim 8, wherein the probe is an ultrasound probe.

10. The method according to claim 9, wherein the probe and the marking device are automatically conveyed by the same apparatus.

11. The method according to claim 10, wherein the tray is removed from the apparatus after the information is collected and placed in the apparatus after the locations of interest have been identified.

12. The method according to claim 11, wherein a radiologist:
uses a computing facility having a screen to view an ultrasound image of the tissue sample; and
makes, on the screen and with one or more of a mouse, stylus, keyboard or touchscreen interface, selections, each selection being a structure which resembles a lymph node.

13. The method according to claim 12, wherein the computing facility generates the locations of interest based upon the selections.

14. The method according to claim 8, wherein the tray is placed in the apparatus after the sample is immobilized.

15. The method according to claim 8, wherein
the probe is an ultrasound probe;
the probe and the marking device are automatically conveyed by the same apparatus;
the tray is removed from the apparatus after the information is collected and placed in the apparatus after the locations of interest have been identified;
a radiologist: uses a computing facility having a screen to view an ultrasound image of the tissue sample; and makes, on the screen and with one or more of a mouse, stylus, keyboard or touchscreen interface, selections, each selection being a structure which resembles a lymph node; and
the computing facility generates the locations of interest based upon the selections.

* * * * *